US006613541B1

(12) United States Patent
Vaddi et al.

(10) Patent No.: US 6,613,541 B1
(45) Date of Patent: Sep. 2, 2003

(54) METHOD FOR MONITORING PROTEASOME INHIBITOR DRUG ACTION

(75) Inventors: Gopalakrishna R. Vaddi, Hockessin, DE (US); Ross L. Stein, Sudbury, MA (US); Lawrence R. Dick, Natick, MA (US); Vito J. Palombella, Needham, MA (US); Eric S. Lightcap, Natick, MA (US); Peter J. Elliott, Marlboro, MA (US); Julian Adams, Brookline, MA (US); Teresa A. McCormack, Medford, MA (US); Stephen J. Brand, Lincoln, MA (US); Dan R. Burns, Skillman, NJ (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/419,551

(22) Filed: Oct. 19, 1999

Related U.S. Application Data

(60) Provisional application No. 60/131,381, filed on Apr. 28, 1999, and provisional application No. 60/104,918, filed on Oct. 20, 1998.

(51) Int. Cl.$^7$ ................................................ C12Q 1/37
(52) U.S. Cl. ........................ 435/23; 435/24; 435/69.2
(58) Field of Search ............................ 435/23, 24, 226, 435/69.2; 548/541

(56) References Cited

U.S. PATENT DOCUMENTS

| 5,340,736 A | * | 8/1994 | Goldberg | |
|---|---|---|---|---|
| 5,574,017 A | | 11/1996 | Gutheil ........................ | 514/19 |
| 5,714,471 A | * | 2/1998 | Rowe et al. | |
| 5,756,764 A | * | 5/1998 | Fenteany et al. | |
| 5,990,083 A | | 11/1999 | Iqbal et al. .................... | 514/9 |

FOREIGN PATENT DOCUMENTS

| WO | WO 94/17816 | 8/1994 | .......... A61K/37/00 |
|---|---|---|---|
| WO | WO 95/24914 | 9/1995 | .......... A61K/38/00 |
| WO | WO 95/25533 | 9/1995 | .......... A61K/38/06 |
| WO | WO 96/32105 | 10/1996 | .......... A61K/31/395 |
| WO | WO 99/22729 | 5/1999 | .......... A61K/31/40 |
| WO | WO 99/43346 | 9/1999 | .......... A61K/38/51 |

OTHER PUBLICATIONS

WO 96/13266. Adams et al. (May 1996). Boronic ester and acid compounds, synthesis and uses.*
WO 91/13904. Siman et al. (Sep. 1991). Chymotrypsin–like proteases and their inhibitors.*
Bogyo et al. "Covalent modification of the active site threonine of proteasomal β subunits and the *Escherichia coli* homolog HsIV by a new class of inhibitors" *Proc. Natl. Acad. Sci. USA*, vol. 94, pp. 6629–6634 (1997).
Ciechanover, Aaron, "The Ubiquitin–Proteasome Proteolytic Pathway" *Cell*, vol. 79, pp. 13–21 (1994).

Coux, et al., "Structure and functions of the 20S and 26S proteasomes" *Annu. Rev. Biochem.*, vol. 65, pp. 801–847 (1996).
Deshaies, Raymond J., "Make it or break it the role of ubiquitin–dependent proteolysis in cellular regulation" *Trends in Cell Biol.*, pp. 428–434 (1995).
Driscoll and Goldberg, "The Proteasome (Multicatalytic Protease) Is a Component of the 1500–kDa Proteotytic Complex Which Degrades Ubiquitin–conjugated Proteins" *The Journal of Biological Chem.*, vol. 285, No. 9, pp. 4789–4792 (1990).
Fenteany, et al., "A β–lactone related to lactacystin induces neurite outgrowth in a neuroblastoma cell line and inhibits cell cycle progression in an osteosarcoma cell line" *Proc. Natl. Acad. Sci. USA*, vol. 91, pp. 3358–3362 (1994).
Fotino, et al., Micromethod for Rapid Separation of Lymphocytes from Peripheral Blood *Ann. of Clinical Lab. Sci.*, vol. 1, No. 2, pp. 131–133 (1971).
Goldberg et al., "New insight into proteasome function: from archaebacteria to drug development" *Chemistry & Biology*, vol. 2, pp. 503–508 (1995).
González, et al., "Proteasome Activity Is Required for the Stage–specific Transformation of a Protozoan Parasite" *J. Exp. Med.*, vol. 184, pp. 1909–1918 (1996).
Hoyt, M. Andrew, "Eliminating All Obstacles: Regulated Proteolysis in the Eukaryotic Cell Cycle" *Cell*, vol. 91, pp. 149–151 (1997).
Iqbal, et al., "Potent Inhibitors of Proteasome" *J. Med. Chem.*, vol. 38, pp. 2276–2277 (1995).
Khan, et al., "Identification and purification of a 90–kDa membrane–bound endogenous inhibitor of multicatalytic proteinase from human erythrocytes" *Biochem. and Biophys. Res. Comm.*, vol. 214, No. 3, pp. 957–962 (1995).
McCormack et al., "Kinetic Studies of the Branched Chain Amino Acid Preferring Peptidase Activity of the 20S Proteasome: Development of a Continuous Assay and Inhibition by Tripeptide Aldehydes and clasto–Lactacystine β–Lactone" *Biochemistry*, vol. 37, pp. 7792–7800 (1998).
Orlowski, et al., "Evidence of the Presence of Five Distinct Proteolytic Components in the Pituitary Multicatalytic Proteinase Complex. Properties of Two Components Cleaving Bonds on the Carboxyl Side of Branched Chain and Small Neutral Amino Acids" *Biochemistry*, vol. 32, pp. 1563–1572 (1993).
Rickwood, et al. "Nycodenz: A New Nonionic Iodinated Gradient Medium" *Analytical Biochemistry*, vol. 123, pp. 23–31 (1982).

(List continued on next page.)

Primary Examiner—Ralph Gitomer
(74) Attorney, Agent, or Firm—Millennium Pharmaceuticals, Inc.

(57) ABSTRACT

The invention relates to methods for measuring proteasome activity in biological samples. More particularly, then invention relates to methods for monitoring drug action following in vivo administration of a proteasome inhibitor. The invention provides methods and kits for monitoring pharmacodynamic drug action and for determining dose regimen for a proteasome inhibitor. The invention also provides methods for determining baseline proteasome activity in a mammal.

30 Claims, 19 Drawing Sheets

OTHER PUBLICATIONS

Spaltenstein, et al., "Design and Synthesis of Novel Protease Inhibitors. Tripeptide α',β'-Epoxyketones as Nanomolar Inactivators of the Proteasome" *Tetrahedron Letters*, vol. 37, No. 9, pp. 1343–1346 (1996).

Tsubuki, et al., "Purification and characterization of an endogenous inhibitor specific to the Z–Leu–Leu–Leu–MCA degrading activity in proteasome and its identification as heat–shock protein 90" *FEBS Letters*, vol. 344, pp. 229–233 (1994).

Wong, H.L., , Mazzola, L.M., Lazarus, D.D., Pien, C.S., Adams, J., and Elliott, Peter J., "Proteasome Inhibitors as New Anti–Cancer Agents: Biological Activity and In Vivo Detection Assay," published abstract, American Association of Cancer Research Conference—Mar. 28–Apr. 1, 1998.

Palombella, Vito "MG341 Inhibits 20S Proteasome Activity in PG/PS Treated Rats," slide from oral presentation, National Managed Health Care Congress, San Diego, Feb. 1997. No abstracts slides or text from this presentation were published or distributed.

* cited by examiner

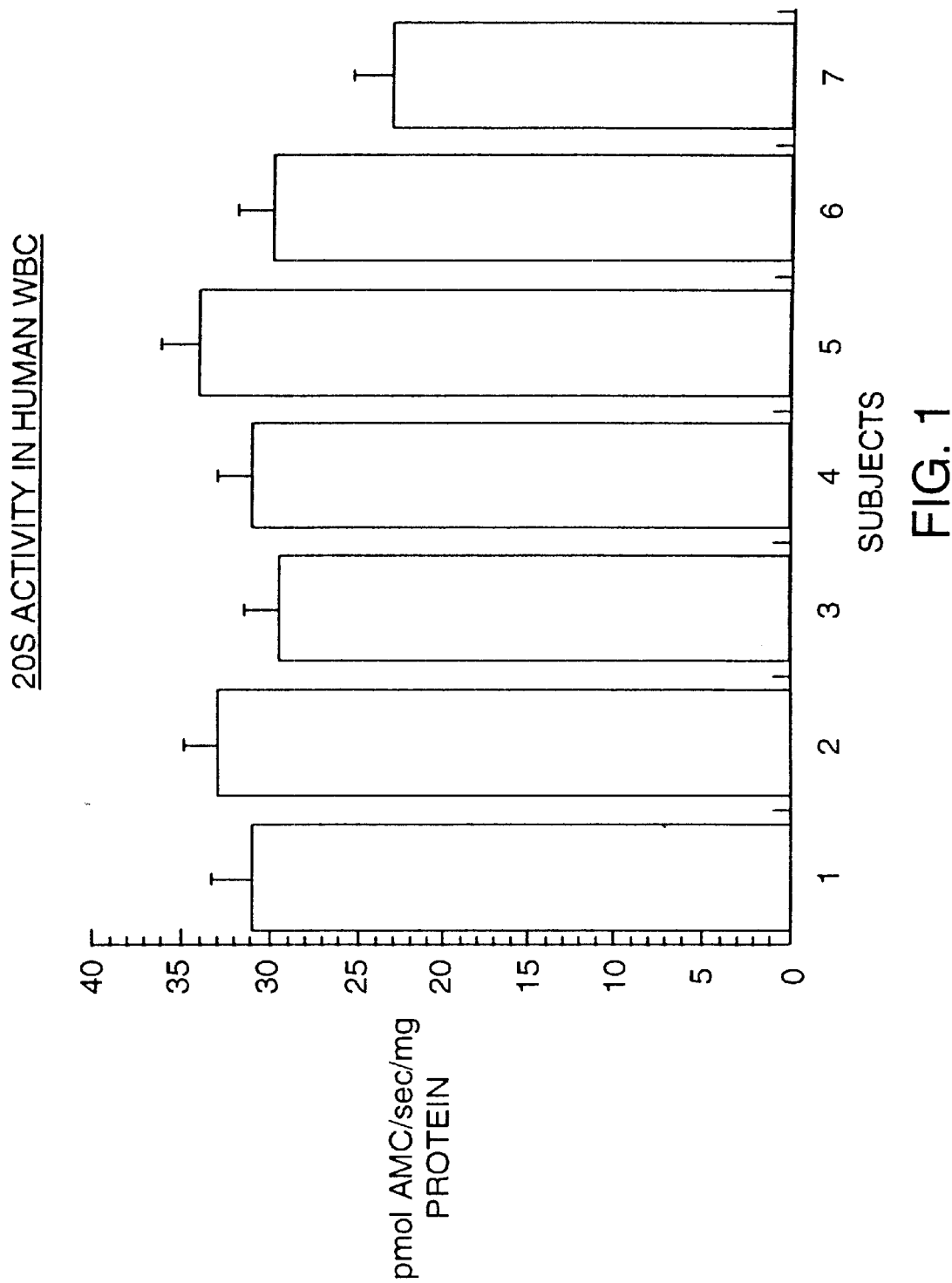

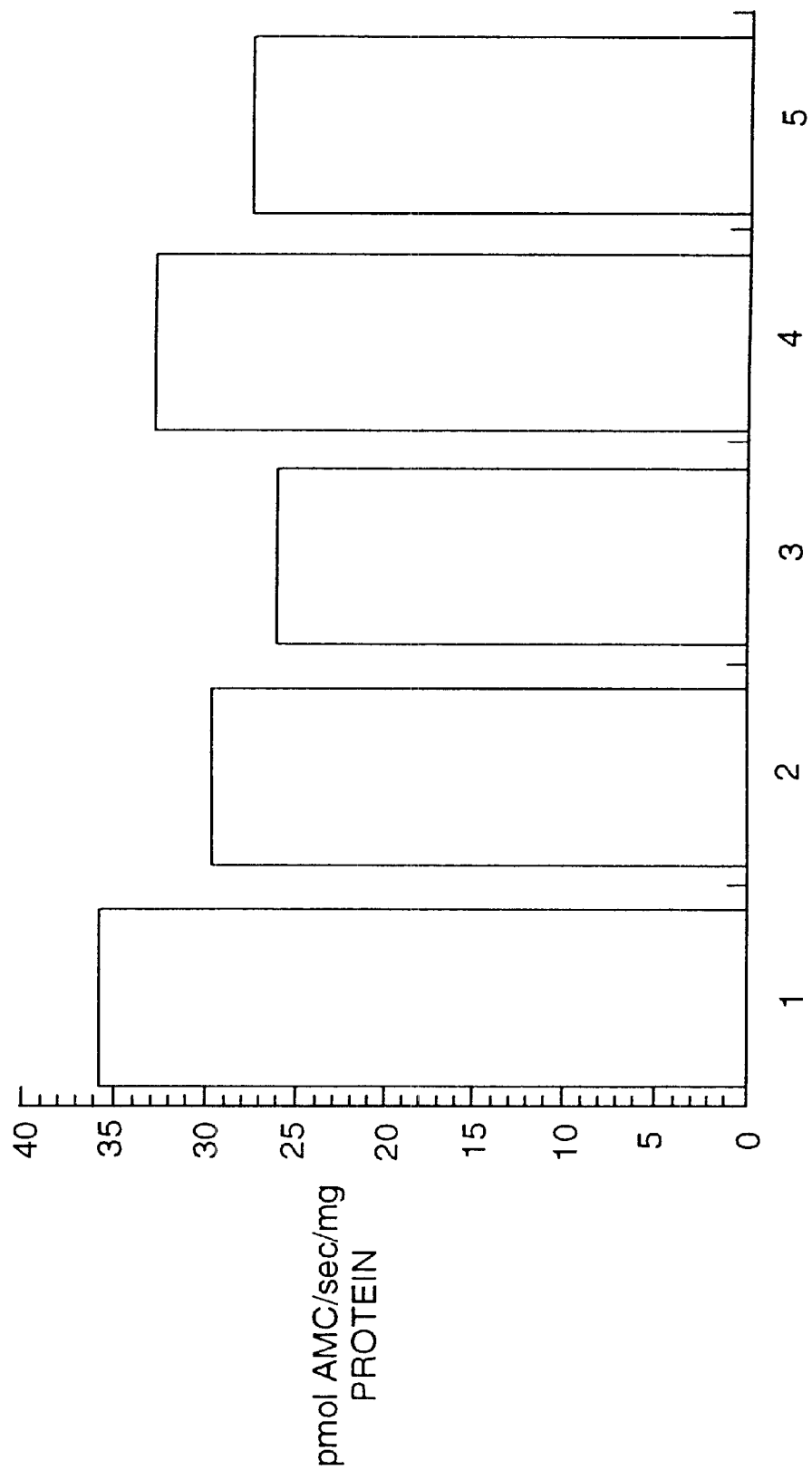

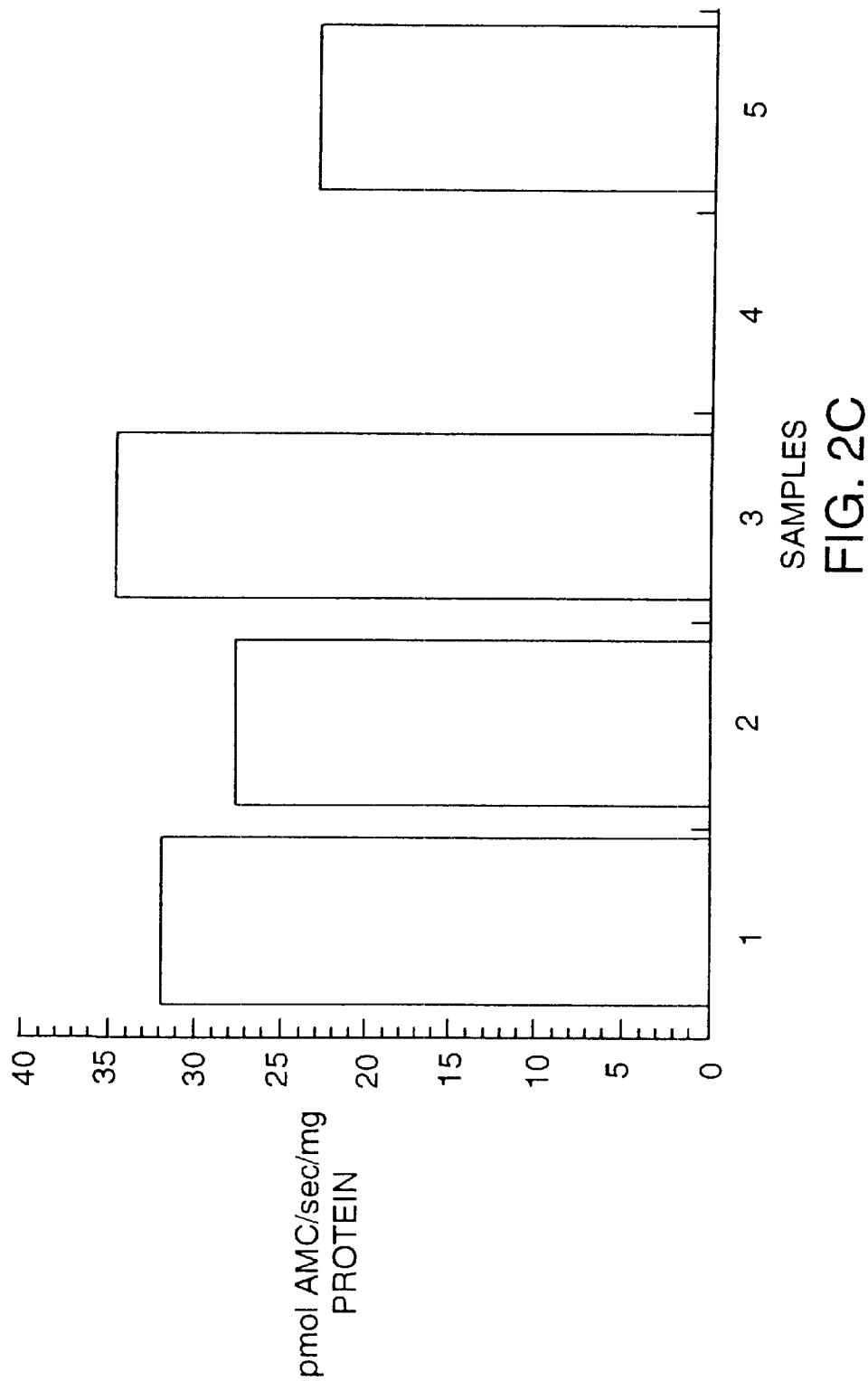

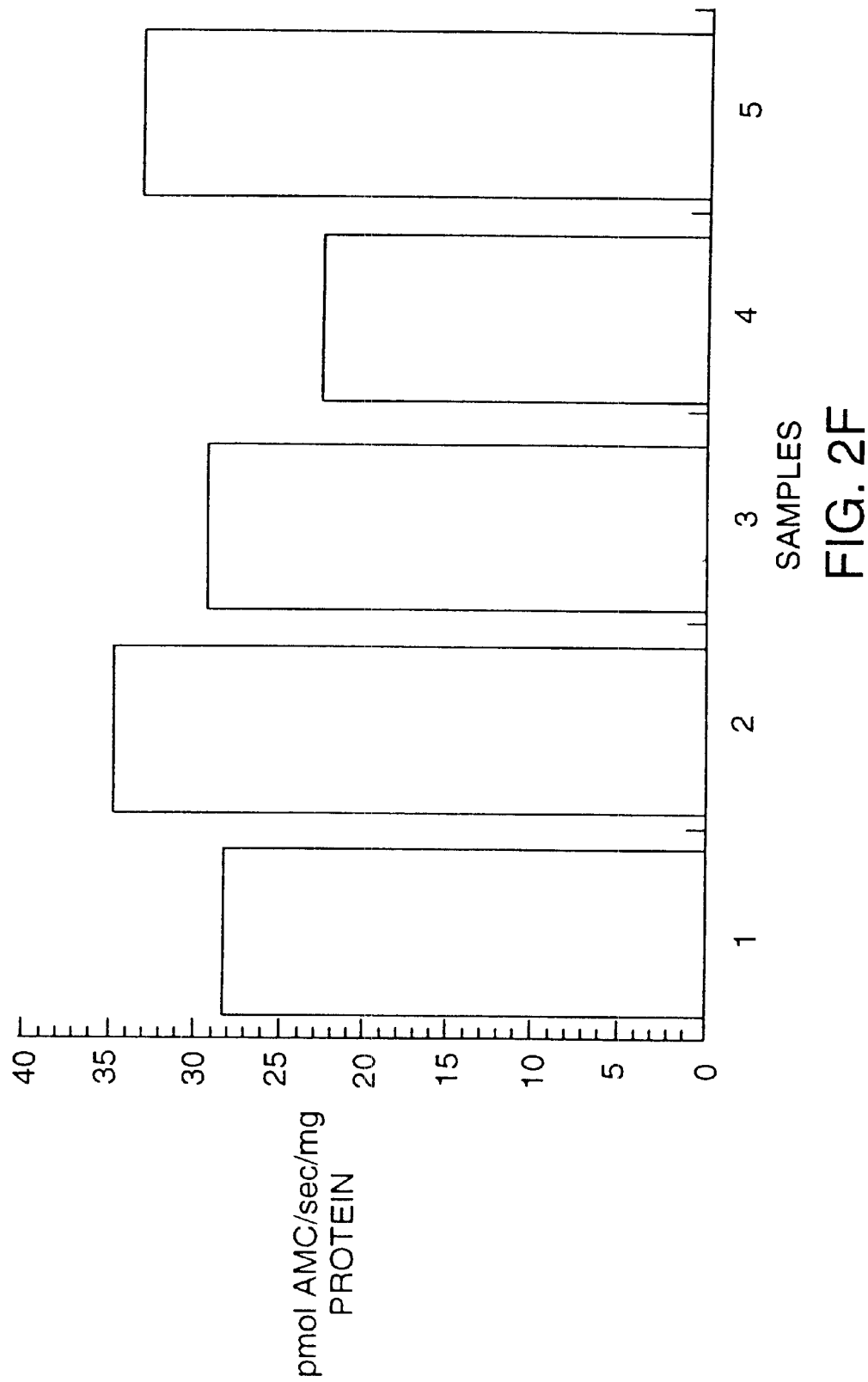

METHOD FOR MONITORING PROTEASOME INHIBITOR DRUG ACTION

CROSS-REFERENCE TO RELATED APPLICATIONS

This application is a nonprovisional patent application claiming priority from provisional patent applications Ser. No. 60/104,918, filed on Oct. 20, 1998, and Ser. No. 60/131,381, filed on Apr. 28, 1999.

BACKGROUND OF THE INVENTION

1. Field of the Invention

This invention relates to methods for measuring proteasome activity in biological samples. More particularly, the invention relates to methods for monitoring drug action following in vivo administration of a proteasome inhibitor.

2. Summary of the Related Art

The 26S proteasome is the multi-catalytic protease responsible for the majority of intracellular protein turnover in eukaryotic cells, including proteolytic degradation of damaged, oxidized or misfolded proteins, as well as processing or degradation of key regulatory proteins required for various cellular function (Ciechanover, Cell 79: 13–21 (1994); Coux et al., Ann. Rev. Biochem. 65:801–847 (1995); Goldberg et al., Chemistry & Biology 2:503–508 (1995)). Protein substrates are first marked for degradation by covalent conjugation to multiple molecules of a small protein, ubiquitin. The resultant polyubiquitinated protein is then recognized and degraded by the 26S proteasome.

Constituting the catalytic core of the 26S proteasome is the 20S proteasome, a multi-subunit complex of approximately 700 kDa molecular weight. Coux et al. (Ann. Rev. Biochem. 65:801–847 (1995)) teaches that the 20S proteasome does not by itself degrade ubiquitinated proteins, but does possess multiple peptidase activities. Based on substrate preferences, Coux et al. characterizes these activities as chymotrypsin-like, trypsin-like, post-glutamyl hydrolase, branched chain amino acid preferring, and small neutral amino acid preferring. Coux et al. also teaches that a dramatic activation of 20S proteasome activity can be induced by various in vitro treatments, such as heating to 55° C., incubation with basic polypeptides, sodium dodecyl sulfate (SDS), guanidine HCl or fatty acids, dialysis against water, or by physiological regulators such as PA28 or PA700. McCormack et al. (Biochemistry 37:7792–7800 (1998)) teaches that a variety of peptide substrates, including Suc-Leu-Leu-Val-Tyr-AMC, Z-Leu-Leu-Arg-AMC, and Z-Leu-Leu-Glu-2NA, wherein Suc is N-succinyl, AMC is 7-amino-4-methylcoumarin, and 2NA is 2-naphthylamine, are cleaved by the 20S proteasome.

The ubiquitin-proteasome pathway plays a central role in a large number of physiological processes. Deshaies (Trends in Cell Biol. 5: 428–434 (1995)) and Hoyt (Cell 91:149–151 (1997)) teach that regulated proteolysis of cell cycle proteins, including cyclins, cyclin-dependent kinase inhibitors, and tumor suppressor proteins, is required for controlled cell cycle progression and that proteolysis of these proteins occurs via the ubiquitin-proteasome pathway. Palombella et al., WO 95/25533 teaches that activation of the transcription factor NF-κB, which itself plays a central role in the regulation of genes involved in the immune and inflammatory responses, is dependent upon the proteasome-mediated degradation of an inhibitory protein, IκB-α. Goldberg and Rock, WO 94/17816 discloses that the continual turnover of cellular proteins by the ubiquitin-proteasome pathway plays an essential role in antigen presentation.

While serving an essential physiological role, the ubiquitin-proteasome pathway also mediates the inappropriate or accelerated protein degradation that occurs as a result or cause of pathological conditions such as cancer, inflammatory diseases, or autoimmune diseases, in which these normal cellular processes have become deregulated. In addition, Goldberg (U.S. Pat. No. 5,340,736 (1994)) teaches that the cachexia or muscle wasting associated with conditions such as cancer, chronic infectious diseases, fever, muscle disuse (atrophy), nerve injury, renal failure, and hepatic failure results from an increase in proteolytic degradation by the ubiquitin-proteasome pathway. Gonzales et al. (J. Exp. Med. 184:1909 (1996)) teaches that the cytoskeletal reorganization that occurs during maturation of protozoan parasites is proteasome-dependent.

Inhibition of proteasome activity thus offers a promising new approach for therapeutic intervention in these and other conditions directly or indirectly mediated by the proteolytic function of the proteasome. Goldberg et al. (Chemistry & Biology 2:503–508 (1995)) teaches that proteasome inhibitors block the inflammatory response in vivo in animal models of human disease.

The present inventors are developing proteasome inhibitors for the treatment of inflammatory and autoimmune diseases and cancer. We have found that, when administering a proteasome inhibitor to a mammal, it is essential that the dose regimen be carefully selected so as to avoid excessive proteasome inhibition. Typically, dose regimens for new drug candidates are determined by measuring the concentration of the drug in a biological sample and setting the dose amount and dose frequency so as to achieve the desired drug level (see, e.g., Ritschel, Handbook of Basic Pharmacokinetics, Fourth Edition, Drug Intelligence Publications, Inc., Hamilton, Ill., 1992). The present inventors have discovered that these standard procedures are unsuitable for proteasome inhibitors. There is thus a need in the art for sensitive methods for monitoring proteasome inhibitor drug action.

BRIEF SUMMARY OF THE INVENTION

The invention provides sensitive methods for monitoring proteasome inhibitor drug action. The present inventors have surprisingly discovered that ex vivo assay of proteasome activity, rather than drug concentration, in biological samples provides a useful method for monitoring pharmacodynamic drug action of proteasome inhibitors and that this data provides guidance for selecting a future dose amount and dose frequency of the proteasome inhibitor to be administered in the future.

In a first aspect, the invention provides a method for monitoring pharmacodynamic drug action of a proteasome inhibitor in a mammal, comprising administering the proteasome inhibitor to the mammal; obtaining one or more test biological samples from the mammal at one or more specified times after administering the proteasome inhibitor; measuring proteasome activity in the test biological sample or samples; determining the amount of proteasome activity in the test biological sample or samples; and comparing the amount of proteasome activity in the test biological sample to that in a reference biological sample obtained from a mammal to which no proteasome inhibitor has been administered.

In a second aspect, the invention provides a method for determining dose regimen for a proteasome inhibitor, comprising administering the proteasome inhibitor to the mammal; obtaining one or more test biological samples from the mammal at one or more specified times after administering the proteasome inhibitor; measuring proteasome activity in the test biological sample or samples; determining the amount of proteasome activity in the test biological sample or samples; comparing the amount of proteasome activity in the test biological sample to that in a reference biological sample obtained from a mammal to which no proteasome inhibitor has been administered; and selecting a dose amount and dose frequency of the proteasome inhibitor to be administered in the future.

In a third aspect, the invention provides a method for determining baseline proteasome activity in a mammal, including a human, comprising obtaining one or more biological samples from the mammal; measuring proteasome activity in the biological sample or samples; and determining the amount of proteasome activity in the biological sample or samples. In one preferred embodiment, the mammal suffers from a disease or pathological condition. In another preferred embodiment, the mammal has been administered a drug. In certain embodiments, the method further comprises determining a dose amount and dose frequency of a proteasome inhibitor to be administered to the mammal.

In a fourth aspect, the invention provides a kit for measuring proteasome activity in a biological sample from a mammal, the kit comprising means for preparation of the biological sample and means for measuring proteasome activity. In certain preferred embodiments, the mammal is a human. In certain other preferred embodiments, the biological sample is a blood, urine, or tissue biopsy sample.

BRIEF DESCRIPTION OF THE DRAWINGS

FIG. 1 is a graphical representation of 20S proteasome activity in white blood cells from 7 human volunteers.

DETAILED DESCRIPTION OF THE PREFERRED EMBODIMENTS

Figure 2B:
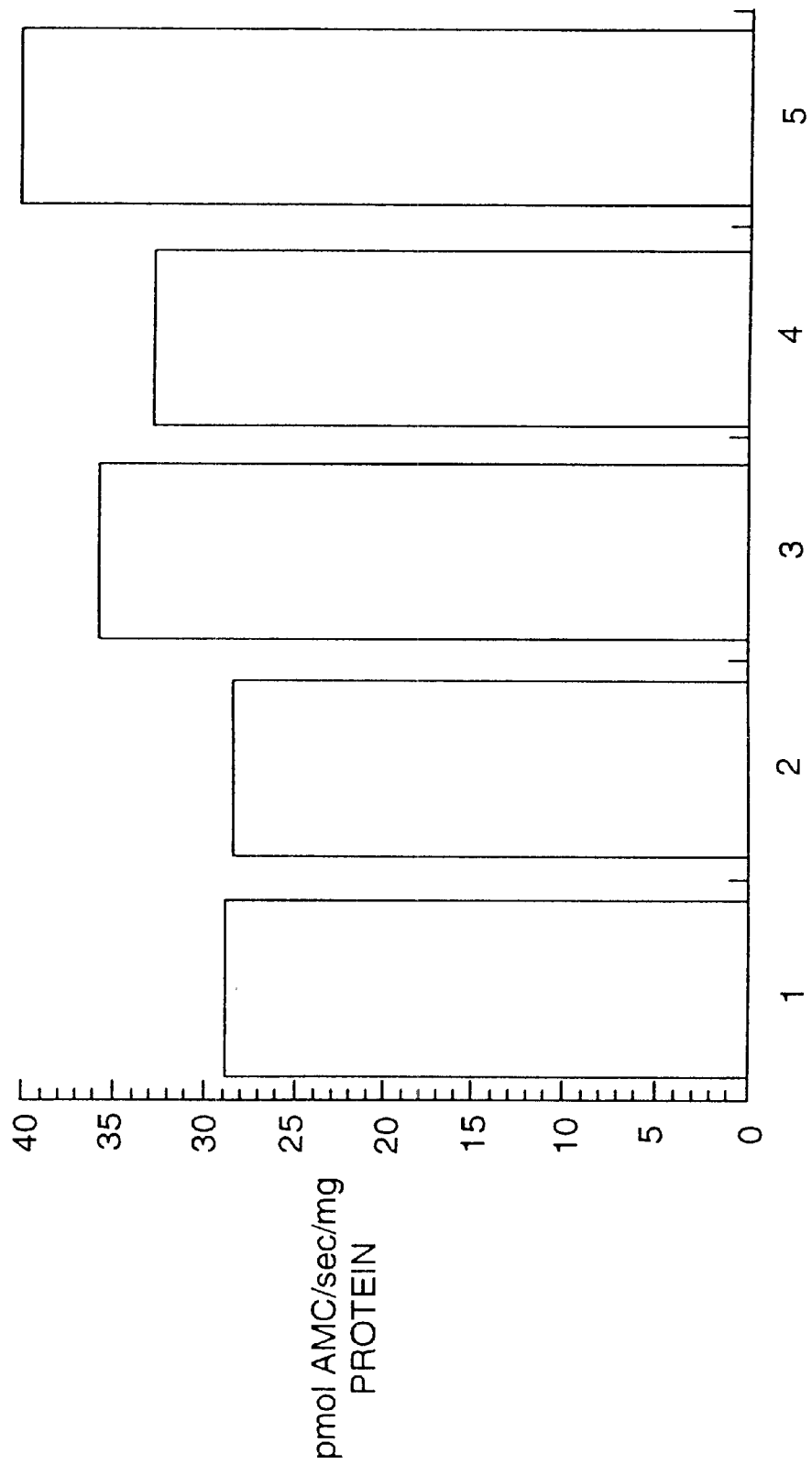
FIG. 2 is a graphical representation of daily 20S proteasome activity in white blood cells from human volunteers
Figure 2D:
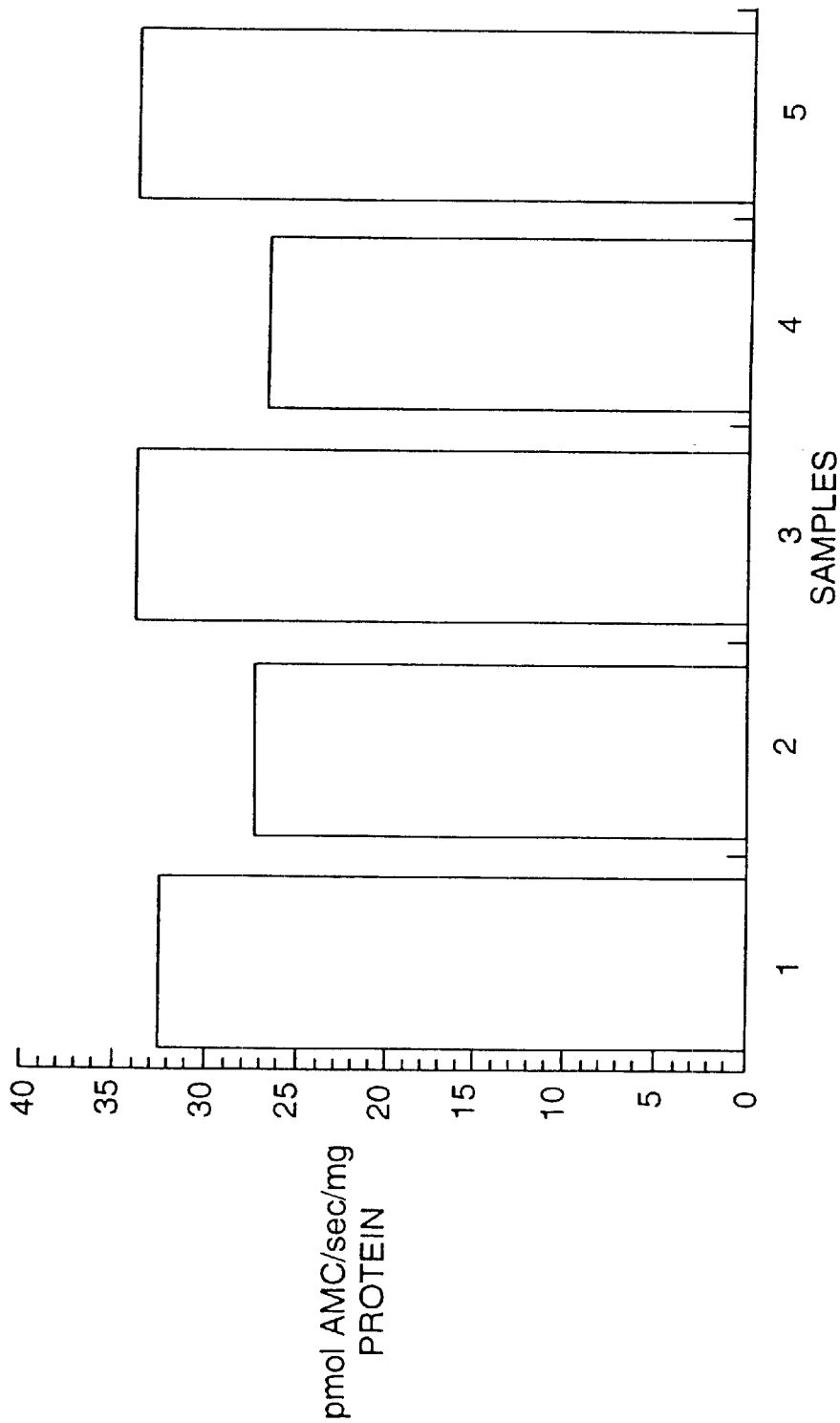
Figure 2E:
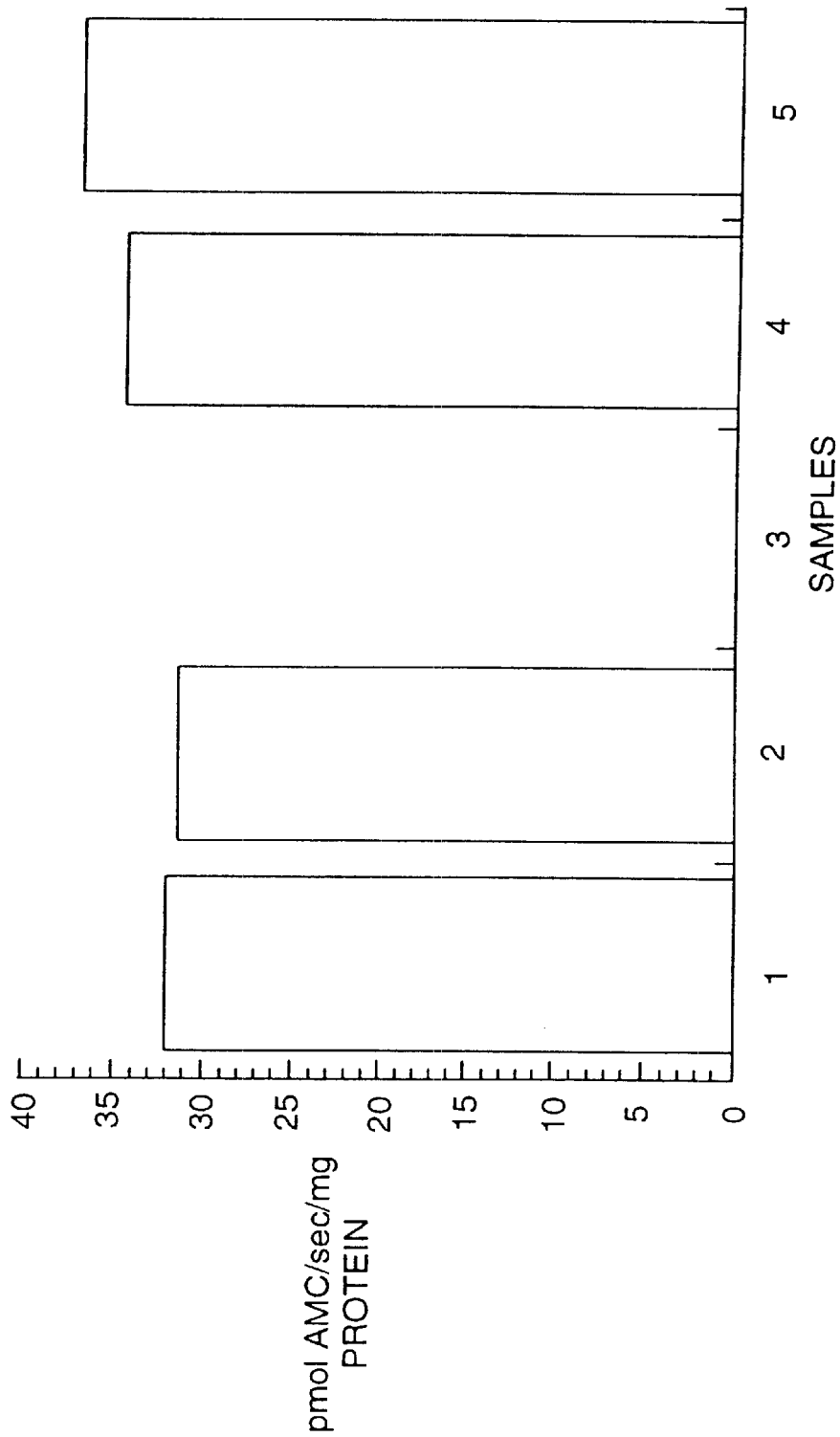
Figure 2G:
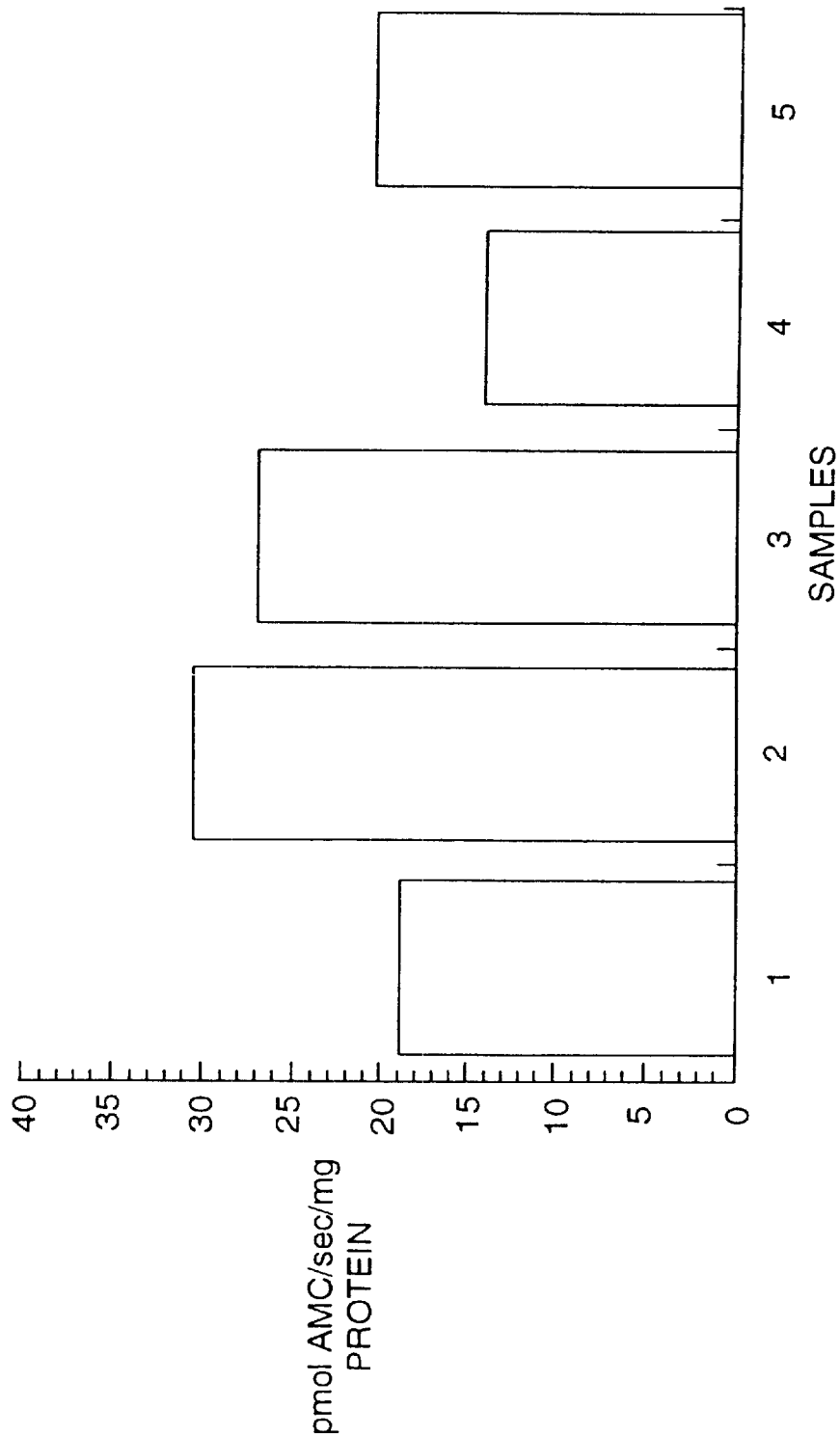

The present invention relates to methods for measuring proteasome activity in biological samples. More particularly, the invention relates to methods for monitoring drug action following in vivo administration of a proteasome inhibitor. The patent applications, patents and literature references cited herein indicate the knowledge in this field and are hereby incorporated by reference in their entirety. In the case of inconsistencies, the present disclosure will prevail.

The present inventors have surprisingly discovered that ex vivo assay of proteasome activity, rather than drug concentration, in biological samples provides a useful method for monitoring pharmacodynamic drug action of proteasome inhibitors and that this data provides guidance for selecting a future dose amount and dose frequency of the proteasome inhibitor to be administered in the future.

The invention provides sensitive methods for monitoring proteasome inhibitor drug action. Proteasome inhibitors are promising new therapeutic agents for treatment of conditions mediated directly by the proteolytic function of the proteasome, such as muscle wasting, or mediated indirectly via proteins which are processed or degraded by the proteasome, such as the transcription factor NF-κB and cell cycle regulatory proteins. The present inventors have demonstrated the in vivo efficacy of proteasome inhibitors in a number of animal tumor models and models of inflammation. However, the present inventors have also found that excessive proteasome inhibition results in toxic effects, including lethality. While not wishing to be bound by theory, the present inventors believe that these toxic effects are predominantly mechanism-based and stem from the pleiotropic nature of proteasome function.

Safe administration of proteasome inhibitors thus requires close monitoring of drug levels and careful selection of the dose regimen so as to prevent an overdose. Typically in the art, drug levels are monitored by measuring the amount of the parent drug and/or its metabolites in the plasma (see, e.g., Ritschel, Handbook of Basic Pharmacokinetics, Fourth Edition, Drug Intelligence Publications, Inc., Hamilton, Ill., 1992). Measurement of drug levels as a function of time provides the pharmacokinetic profile of the drug, from which parameters such as maximal concentration ($C_{max}$), half-life ($t_{1/2}$), area under the curve (AUC), and volume of distribution ($V_d$). However, the present inventors have found that.these standard methods are not suitable for use with proteasome inhibitors. Within minutes after intravenous administration of a therapeutic dose of a proteasome inhibitor in an animal, the drug is virtually undetectable in the plasma compartment. Without wishing to be bound by theory, the present inventors believe that the proteasome inhibitor is rapidly sequestered by intracellular proteasomes in the vasculature and in tissues. Measurement of circulating drug in the plasma thus grossly underestimates the amount of bioactive drug present. Alternative methods that more accurately reflect the true pharmacodynamic profile of proteasome inhibitors are thus urgently needed.

For purposes of the present invention, the following definitions will be used:

"Proteasome inhibitor" shall mean any substance which directly or indirectly inhibits the 20S or 26S proteasome or the activity thereof. Preferably, such inhibition is specific, i.e., the proteasome inhibitor inhibits proteasome activity at a concentration that is lower than the concentration of the inhibitor required to produce another, unrelated biological effect. Preferably, the concentration of the proteasome inhibitor required for proteasome inhibition is at least 2-fold lower, more preferably at least 5-fold lower, even more preferably at least 10-fold lower, and most preferably at least 20-fold lower than the concentration required to produce an unrelated biological effect. Non-limiting examples of proteasome inhibitors for use in the present invention include peptide aldehydes (see, e.g., Stein et al. WO 95/24914 published Sep. 21, 1995; Siman et al. WO 91/13904 published Sep. 19, 1991; Iqbal et al. J. Med. Chem. 38:2276–2277 (1995)), vinyl sulfones (see, e.g., Bogyo et al., Proc. Natl. Acad. Sci. 94:6629 (1997)), $\alpha'\beta'$-epoxyketones (see, e.g., Spaltensteinet al. Tetrahedron Lett. 37:1343 (1996)); peptide boronic acids (see, e.g., Adams et al. WO 96/13266 published May 9, 1996; Siman et al. WO 91/13904published Sep. 19, 1991), and lactacystin and lactacystin analogs (see, e.g., Fenteany et al. Proc. Natl. Acad. Sci. USA 94:3358 (1994); Fenteany et al. WO 96/32105 published Oct. 19, 1996), each of which is hereby incorporated by reference in its entirety.

"Biological sample" shall mean any body fluid, organ, or tissue sample obtained from an animal. The animal may be dead or alive at the time the sample is obtained. The animal is preferably a mammal, which term is meant to include humans.

"Test biological sample" shall mean a biological sample that is obtained from an animal to which a proteasome inhibitor has been administered.

"Reference biological sample" shall mean a biological sample that is obtained from an animal to which no proteasome inhibitor has been administered, including a statistical or historical reference sample which has been prepared or preserved in written, readable or electronic form. "Readable form" includes any form which may be understood to have a particular meaning to a machine or a technician.

"Standard sample" shall mean a sample comprising a known or constant amount of 20S or 26S proteasome activity. The sample may comprise purified or partially purified proteasomes, or it may comprise a biological sample that contains proteasomes.

"Proteasome activity" shall mean any proteolytic or peptidase activity associated with the 26S or 20S proteasome.

"Peptide" shall mean a molecule comprised of a linear array of amino acid residues connected to each other in the linear array by peptide bonds. Such peptides according to the invention may include from about three to about 500 amino acids, and may further include secondary, tertiary or quaternary structures, as well as intermolecular associations may be through, without limitation, covalent bonding (e.g., through disulfide linkages), or through chelation, electrostatic interactions, hydrophobic interactions, hydrogen bonding, ion-dipole interactions, dipole-dipole interactions, or any combination of the above.

In a first aspect, the invention provides a method for monitoring pharmacodynamic drug action of a proteasome inhibitor in a mammal, comprising administering the proteasome inhibitor to the mammal; obtaining one or more test biological samples from the mammal at one or more specified times after administering the proteasome inhibitor; measuring proteasome activity in the test biological sample or samples; determining the amount of proteasome activity in the test biological sample or samples; and comparing the amount of proteasome activity in the test biological sample to that in a reference biological sample obtained from a mammal to which no proteasome inhibitor has been administered.

The biological samples that are obtained from the mammal may include, without limitation, blood, urine, organ, and tissue samples. Preferably, the biological sample according to this aspect of the invention is a blood sample, more preferably a blood cell lysate. Cell lysis may be accomplished by standard procedures. In certain preferred embodiments, the biological sample is a whole blood cell lysate. Kahn et al. (*Biochem. Biophys. Res. Commun.*, 214:957–962 (1995)) and Tsubuki et al. (*FEBS Lett.*, 344:229–233 (1994)) disclose that red blood cells contain endogenous proteinaceous inhibitors of the proteasome. Thus, contamination of biological samples with even small amounts of red blood cells could interfere with the assay. However, the present inventors have found that the endogenous proteasome inhibitors are inactivated in the presence of SDS at a concentration of about 0.05%, allowing red blood cell lysates and whole blood cell lysates to be assayed reliably. At this concentration of SDS, all proteasome activity is due to the 20S proteasome. Although purified 20S proteasome exhibits poor stability at 0.05% SDS, 20S proteasome activity in cell lysates is stable under these conditions. The ability to perform the assay in whole blood cell lysates offers significant advantages in terms of economy and ease of sample preparation.

In certain other preferred embodiments, the biological sample is a white blood cell lysate. Methods for fractionating blood cells are known in the art (Rickwood et al., Anal. Biochem. 123:23–31 (1982); Fotino et al., Ann. Clin. Lab. Sci. 1:131 (1971)) and are further described in the Examples. Commercial products useful for cell separation include without limitation Ficoll-Paque® (Pharmacia Biotech) and NycoPrep (Nycomed). In some situations, white blood cell lysates provide better reproducibility of data than do whole blood cell lysates and, therefore, may be preferred in those situations.

Variability in sample preparation can be corrected for by introducing a normalization step into he workup of the data. In certain preferred embodiments, proteasome activity in the sample may be normalized relative to the protein content in the sample (specific activity method). Total protein content in the sample can be determined using standard procedures, including, without limitation, Bradford assay and the Lowry method. In certain other preferred embodiments, proteasome activity in the sample may be normalized relative to cell count. This embodiment may be preferred in settings, such as clinical settings, in which automated cell counters are readily accessible.

Proteasome inhibitors often exhibit preferential inhibition of one peptidase activity of the proteasome over other proteasome peptidase activities. The present inventors have recognized that this differential inhibition provides an alternative approach to normalization procedures based on protein content or cell count. Thus, in certain particularly preferred embodiments, proteasome inhibition is determined as a ratio of one peptidase activity of the proteasome to another. The derivation of the theoretical equation for determination of proteasome inhibition according to this embodiment of the invention is provided in the Examples. In order for this embodiment of the invention to be operative, the proteasome inhibitor under study must inhibit one peptidase activity preferentially over at least one other peptidase activity. Selection of the peptidase activities to be assayed, and thus the appropriate peptidic substrates to be used, will depend on the inhibitor under study. For example, for the inhibitor N-(pyrazine)carbonyl-L-phenylalanine-L-leucine boronic acid (1), proteasome inhibition is preferably determined as a ratio of chymotryptic activity to tryptic activity. Chymotryptic activity is fully inhibitable by 1, whereas tryptic activity is activated by 1 over the same concentration range.

The mammal from which the biological samples are obtained is preferably a rat, mouse, dog, pig, rabbit, non-human primate, or human. Non-human primates include, without limitation, cynomolgus monkeys, tamarins, chimpanzees, and baboons. More preferably, the mammal is a human, most preferably a human undergoing therapeutic treatment with a proteasome inhibitor. Treatment may occur in a hospital setting or on an out-patient basis. Preferably, the human is a patient suffering from a condition resulting from ubiquitin-proteasome pathway mediated inappropriate or accelerated protein degradation. In preferred embodiments, such condition is selected from the group consisting of HIV infection; cachexia; protozoan parasitic diseases such as malaria; cell proliferative diseases such as cancer, psoriasis, and restenosis; and inflammatory diseases. Inflammatory diseases include, without limitation, osteo- and rheumatoid arthritis; inflammatory bowel disease, including ulcerative colitis and Crohn's disease; sepsis; transplant rejection; asthma; and ischemia or reperfusion injury, including stroke and myocardial infarction. In certain preferred embodiments, the human is a cancer patient or a patient suffering or at risk for developing ischemia or reperfusion injury.

Peptide aldehyde proteasome inhibitors for use in the present invention preferably include those disclosed in Stein et al. WO 95/24914 published Sep. 21, 1995, or Siman et al. WO 91/13904 published Sep. 19, 1991, both hereby incorporated by reference in their entirety.

Boronic acid or ester compounds for use in the present invention preferably include those disclosed in Adams et al. WO/9613266 published May 9, 1996, or Siman et al. WO 91/13904 published Sep. 19, 1991, both of which are hereby incorporated by reference in their entirety.

More preferably, the boronic acid compound for use in the present invention is selected from the group consisting of:

N-acetyl-L-leucine-β-(1-naphthyl)-L-alanine-L-leucine boronic acid;

N-(8-quinoline)sulfonyl-β-(1-naphthyl)-L-alanine-L-leucine boronic acid;

N-(pyrazine)carbonyl-L-phenylalanine-L-leucine boronic acid;

β-(1-naphthyl)-L-alanine-L-leucine boronic acid; and

N-(4-morpholine)carbonyl-[O-(2-pyridylmethyl)]-L-tyrosine-L-leucine boronic acid.

Lactacystin and lactacystin analog compounds for use in the present invention preferably include those disclosed in Fenteany et al. WO 96/32105 published Oct. 17, 1996, hereby incorporated by reference in its entirety. More preferably, the lactacystin analog is selected from lactacystin, clasto-lactacystin β-lactone, 7-ethyl-clasto-lactacystin β-lactone and 7-n-propyl-clasto-lactacystin β-lactone. Most preferably, the lactacystin analog is 7-n-propyl-clasto-lactacystin β-lactone.

The proteasome inhibitor may be administered to the mammal by any route, including intradermally, intraperitoneally, subcutaneously, intraarticularly, orally, intratracheally, intranasally, intraarterially, intravenously, topically, or rectally. In certain preferred embodiments, the proteasome inhibitor may be administered intratumorally. Parenteral administrations may be provided in a bolus or by infusion. Administration by the intravenous or intraperitoneal route is presently preferred. The proteasome inhibitor may be administered in a single dose or in repeat doses. Repeat doses may be administered at a frequency ranging from once monthly to several times daily. As discussed below, the methods of the invention are useful for determining the dose amount and frequency that is appropriate for a particular proteasome inhibitor.

Proteasome activity in the biological sample is measured by any assay method suitable for determining 20S or 26S proteasome activity. (See, e.g., McCormack et al., Biochemistry 37:7792–7800 (1998)); Driscoll and Goldberg, J. Biol. Chem. 265:4789 (1990); Orlowski et al., Biochemistry 32:1563 (1993)). Preferably, a substrate having a detectable label is provided to the reaction mixture and proteolytic cleavage of the substrate is monitored by following disappearance of the substrate or appearance of a cleavage product. Detection of the label may be achieved, for example, by fluorometric, colorimetric, or radiometric assay.

Preferred substrates for determining 26S proteasome activity include, without limitation, lysozyme, α-lactalbumin, β-lactoglobulin, insulin b-chain, and ornithine decarboxylase. When 26S proteasome activity is to be measured, the substrate is preferably ubiquitinated or the reaction mixture preferably further comprises ubiquitin and ubiquitination enzymes.

More preferably, the substrate is a peptide less than 10 amino acids in length. In one preferred embodiment, the peptide substrate contains a cleavable fluorescent label and release of the label is monitored by fluorometric assay. Non-limiting examples of preferred substrates according to this embodiment of the invention include N-(N-carbobenzyloxycarbonylleucylleucylarginyl)-7-amino-4-methylcoumarin (Z-Leu-Leu-Arg-AMC), N-(N-benzoylvalylglycylarginyl)-7-amino-4-methylcoumarin (Bz-Val-Gly-Arg-AMC), N-(N-carbobenzyloxycarbonylleucylleucylarginyl)-2-naphthylamine (Z-Leu-Leu-Glu-2NA), or N-(N-succinylleucylleucylvalyltyrosyl)-7-amino-4-methylcoumarin (Suc-Leu-Leu-Val-Tyr-AMC). In certain preferred embodiments, the reaction mixture further comprises a 20S proteasome activator. Preferred activators include those taught in Coux et al. (Ann. Rev. Biochem. 65: 801–847 (1995)), preferably PA28 or sodium dodecyl sulfate (SDS).

Day-to-day variability in the assay may result from factors such as differences in buffer solutions, operator variability, variability in instrument performance, and temperature variability. Such variability can be minimized by standardizing proteasome activity in both the biological sample and the reference sample relative to a standard proteasome sample comprising a known or constant amount of proteasome activity. In certain preferred embodiments, the standard sample comprises purified 20S proteasome, more preferably purified 20S proteasome from a eukaryote. The source of 20S proteasome is not critical and includes without limitation mammals, including without limitation rabbits. In certain preferred embodiments, the 20S proteasome is purified from rabbit reticulocytes. In certain other preferred embodiments, the standard sample is a biological sample, including, without limitation, a blood sample. Preferably, the biological sample is a whole blood cell lysate, more preferably a whole blood cell lysate obtained from a human, preferably a human who has not been exposed to proteasome inhibitor administration.

The proteasome activity measured in the test biological sample is compared to that measured in a reference biological sample obtained from a mammal to which no proteasome inhibitor has been administered. In some preferred embodiments, the test biological sample and the reference biological sample each separately comprise a plurality of samples pooled from a group of mammals, preferably mice, undergoing treatment. In other preferred embodiments, the test biological sample and the reference biological sample each comprise a single sample obtained from an individual mammal. Assaying of individual samples is presently preferred except when impractical due to the small size of the mammal. In some preferred embodiments, a statistical sample is obtained by pooling data from individual test biological samples or from individual reference biological samples.

In some preferred embodiments, the reference sample is obtained from the treated mammal prior to initiation of proteasome inhibitor treatment. This embodiment is presently preferred for higher mammals in order to minimize the impact of inter-mammal variability. Clinical monitoring of proteasome inhibitor drug action presently preferably entails this embodiment of the invention, with each patient serving as his or her own baseline control.

A decrease in proteasome activity in the biological sample as compared to the reference sample is indicative of an in vivo effect of the proteasome inhibitor at the time the biological sample was obtained. In some preferred embodiments, biological samples are obtained at multiple timepoints following administration of the proteasome inhibitor. In these embodiments, measurement of proteasome activity in the biological samples provides an indication of the extent and duration of in vivo effect of the proteasome inhibitor. In certain other preferred embodiments, multiple biological samples are obtained from a single mammal at one or more time points. In these embodiments, measurement of proteasome activity in the biological samples provides an indication of the distribution of the proteasome inhibitor in the mammal.

Potential sources of variability in proteasome activity measurements include inter-individual differences, fluctuations in proteasome activity in a single individual over time, and differences in proteasome activity in white blood cells and red blood cells. All three sources of variability may impact prqteasome inhibition determinations based on specific activity. By contrast, proteasome inhibition determinations based on the ratio of one peptidase activity of the proteasome to another may exhibit greater consistency.

In a second aspect, the invention provides a method for determining dose regimen for a proteasome inhibitor, comprising administering the proteasome inhibitor to the mammal; obtaining one or more test biological samples from the mammal at one or more specified times after administering the proteasome inhibitor; measuring proteasome activity in the test biological sample or samples; determining the amount of proteasome activity in the test biological sample or samples; comparing the amount of proteasome activity in the test biological sample to that in a reference biological sample obtained from a mammal to which no proteasome inhibitor has been administered, and selecting a dose amount and dose frequency of the proteasome inhibitor to be administered in the future.

Preferred embodiments according to this aspect of the invention are as described above for the first aspect.

Dose amount may preferably be determined on a mg/kg or mg/m$^2$ basis. The mammal to which the future dose is to be administered may be the same mammal as that from which the biological sample or samples were obtained, or it may be a different mammal. In some embodiments, the above recited steps may be repeated. For example, in a clinical setting, the dose amount and dose frequency may be repeatedly or continuously adjusted as a result of repeated monitoring of proteasome activity in biological samples obtained from the patient.

In certain preferred embodiments, the dose amount and dose frequency of the proteasome inhibitor are selected so as to avoid excessive proteasome inhibition. In some embodiments, excessive roteasome inhibition results in a toxic effect, the toxic effect including, but not being limited to, vomiting, diarrhea, hypovolemia, hypotension, and lethality. Preferably the dose amount and dose frequency of the proteasome inhibitor are selected so that proteasome inhibition in any future biological sample does not exceed about 95%.

In certain other preferred embodiments, the dose amount and dose frequency of the proteasome inhibitor are selected so that therapeutically useful proteasome inhibition is achieved. Preferably, therapeutically useful proteasome inhibition results in a therapeutically beneficial antitumor, antiinflammatory, antiviral, or antiparasitic effect. Preferably, the dose amount and dose frequency of the proteasome inhibitor are selected so that proteasome inhibition of at least about 15%, preferably about 20%, more preferably about 30%, even more preferably about 40%, still more preferably about 50%, and most preferably from about 50 to about 80% is achieved in a future biological sample, although in some instances proteasome inhibition as high as 95% may be preferred.

In certain preferred embodiments, the biological sample is obtained from a locus of disease. In one preferred embodiment, the biological sample comprises a tumor or tumor cells, preferably from a cancer patient. The biological sample according to this embodiment is preferably obtained by biopsy of a tumor present in the patient. In another preferred embodiment, the biological sample comprises blood cells or blood cell precursors from a patient with a blood cell proliferative disorder. In another preferred embodiment, the biological sample is obtained by skin biopsy of a patient with psoriasis. In another preferred embodiment, the biological sample is obtained by biopsy of the colon of a patient suffering inflammatory bowel disease. In yet another preferred embodiment, the biological sample comprises synovial fluid, preferably from a patient with arthritis. In still another preferred embodiment, the biological sample comprises muscle cells, preferably from a cachectic patient. In still yet another preferred embodiment, the biological sample comprises bronchial fluid, preferably from a patient with asthma.

In a third aspect, the invention provides a method for determining baseline proteasome activity in a mammal, comprising obtaining one or more biological samples from the mammal; measuring proteasome activity in the biological sample or samples; and determining the amount of proteasome activity in the biological sample or samples. In certain embodiments, the method further comprises determining a dose amount and dose frequency of a proteasome inhibitor to be administered to the mammal.

Preferred embodiments according to this aspect of the invention are as described above for the first and second aspects.

In one preferred embodiment according to this aspect of the invention, the mammal suffers from a disease or pathological condition. The present inventors contemplate that in vivo proteasome activity will be altered in certain disease states. It is important that deviations from the normal amount of proteasome activity be identified prior to initiation of treatment with a proteasome inhibitor. Where baseline proteasome activity is higher than normal, a higher than normal dose of proteasome inhibitor may be required. Conversely, where baseline proteasome activity is lower than normal, a lower than normal dose of proteasome inhibitor may be required.

In certain preferred embodiments, proteasome activity data for a biological sample obtained from a mammal suffering from a disease or pathological condition is combined with proteasome activity data for biological samples from other mammals with the same disease or condition. The combined data is then compared to proteasome activity data for a reference biological sample obtained from a mammal or mammals without the disease or condition. The method according to this aspect of the invention allows a statistical determination of the effect, if any, that the disease or condition has on in vivo proteasome activity. In certain preferred embodiments, the method father comprises determining a dose amount and dose frequency of proteasome inhibitor to be administered to a mammal suffering from the disease or pathological condition. The diseased mammal to which the proteasome inhibitor is to be administered may be the same mammal as that for which baseline proteasome activity was determined or it may be a different mammal with the same disease or condition.

In certain other preferred embodiments, the method according to this aspect of the invention further comprises determining a diagnosis or prognosis for the mammal. The inventors contemplate that proteasome activity levels may distinguish between different disease states that give rise to similar symptoms. Similarly, mammals with a particular disease may be divided into subpopulations according to baseline proteasome activity level. The inventors contemplate that the methods of the invention will be useful for correlating baseline proteasome activity levels with disease outcome and for determining the prognosis for an individual mammal based on the correlative data.

In another preferred embodiment, the mammal has been administered a drug. Drugs administered for a variety of purposes may affect proteasome activity levels either directly, e.g., by inhibiting the proteasome, or indirectly, e.g., by affecting metabolic pathways, or affecting substrate availability. The present invention provides methods for monitoring these effects and for predicting drug-drug interactions. In certain preferred embodiments, proteasome activity is measured in a biological sample obtained from a drug-treated mammal prior to initiation of treatment of the mammal with a proteasome inhibitor. The method further comprises determining a dose amount and dose frequency of the proteasome inhibitor to be administered.

In certain other embodiments, proteasome activity data obtained for biological samples obtained from a drug-treated mammal is combined with proteasome activity data for biological samples from other mammals treated with the same drug. The combined data is then compared to proteasome activity data for a reference biological sample obtained from a mammal or mammals which have not been administered the drug. The method according to this aspect of the invention allows a statistical determination of the effect, if any, that the drug has on in vivo proteasome activity. In certain preferred embodiments, the method father comprises determining a dose amount and dose frequency of proteasome inhibitor to be administered to a mammal treated with the drug. The drug-treated mammal to which the proteasome inhibitor is to be administered may be the same mammal as that for which baseline proteasome activity was determined or it may be a different mammal which has also been treated with the same drug.

In a fourth aspect, the invention provides a kit for measuring proteasome activity in a biological sample from a mammal, the kit comprising means for preparation of the biological sample and means for measuring proteasome activity. In certain preferred embodiments, the mammal is a human. In certain other preferred embodiments, the biological sample is a blood, urine, or tissue biopsy sample.

The following examples are intended to further illustrate certain preferred embodiments of the invention and are not limiting in nature.

EXAMPLES

Example 1

Pharmacokinetics of N-(Pyrazine)carbonyl-L-phenylalanine-L-leucine Boronic Acid (1) in Rats and Primates Rats A single dose intravenous pharmacokinetics study with N-(pyrazine) carbonyl-L-phenylalanine-L-leucine boronic acid (1) was conducted in Sprague-Dawley rats (140 to 280 g). Animals were assigned to 3 groups (6/sex in Groups 1 and 2; 9/sex in Group 3). Animals in groups 1, 2, and 3 received 0.03, 0.1 or 0.3 mg/kg of 1, respectively, in the same dose volume.

Blood samples (approximately 1.0 mL) were collected from the jugular vein of animals pre-dose and at approximately 10 and 30 min and 1, 3 and 24 h post-dose on Day 1. The samples were assayed for 1 using a chromatography/mass spectroscopy (LC/MS/MS) method. The lower limit of quantitation for analysis was established at 2.5 ng/mL for 1 in rat plasma and whole blood.

Following the single intravenous doses, plasma or whole blood levels of 1 were only measurable at the 0.3 mg/kg dose level. The observed $C_{max}$ occurred at the first time point; hence, the time to peak concentration ($T_{max}$) was estimated to be $\leq 10$ min in both male and female rats. Males generally had slightly higher peak concentration ($C_{max}$) and area under the concentration-time curve ($AUC_{0-t}$) values than females. The $C_{max}$ values in plasma and in whole blood in males were 51.8 and 22.7 ng/mL, respectively and in females were 36.9 and 19.1 ng/mL, respectively. The $AUC_{0-t}$ values in plasma and whole blood in males were 14.0 and 18.6 ng h/mL, respectively and in females were 12.9 and 17.7 ng h/mL, respectively. Estimation of the elimination half-life ($t_{1/2}$) was not possible due to the fluctuation of 1 levels during the terminal phase. The observations suggest that 1 is rapidly cleared from the blood.

Primates

Levels of 1 in blood and plasma were measured at 2 hours post-dose in a range-finding study in primates. Single intravenous doses of 1 were administered to two cynomolgus monkeys (1 male, 3.3 kg; 1 female, 2.3 kg). Each monkey received two single doses (0.1 mg/kg on Day 1 and 0.3 mg/kg on Day 8) at a dose volume of 1.0 mL/kg. The vehicle was 0.1% ascorbic acid/2% ethanol/98% saline (0.9%). This work was carried out by Covance Laboratories Inc., Madison, Wis.

Following intravenous administration, blood was collected from each animal on Days 1 and 8 at approximately 2 h after dosing. The blood and plasma samples were stored in a freezer set to maintain $-20\pm10°$ C. until analyzed for test material content.

Samples were assayed for 1 using a chromatography/mass spectroscopy (LC/MS/MS) method. The lower limit of quantitation for analysis was established at 2.5 ng/mL for 1 in monkey plasma and whole blood. Two hours following administration of 0.1 mg/kg of 1, concentrations of 1 were less than 2.5 ng/mL (male and female) in plasma; the concentration of 1 in whole blood was 3.72 ng/mL in the male and 3.86 ng/mL in the female. Two hours following administration of 0.3 mg/kg of 1, concentrations of 1 in plasma were 4.64 ng/mL (female) and 6.44 ng/mL (male); concentrations of 1 in whole blood were 10.6 ng/mL (female) and 9.01 ng/mL (male).

Example 2

Preparation of Peripheral White Blood Cell Lysates for in Vitro Measurement of 20S Proteasome Activity This preparation procedure applies to blood samples collected from mammals, particularly rats, mice, dogs, pigs, rabbits, non-human primates, or human subjects. Peripheral white blood cells are separated from blood samples upon collection for storage at about −70° C. until tested. To avoid interference with the assay due to the presence of endogenous proteasome inhibitors, it is important that red blood cells be rigorously excluded.

Procedure

The required amount of blood is collected into a tube containing anticoagulant. For human subjects and primates, approximately 5 mL of blood is required; for rats, approximately 4 mL of blood is needed; for mice, approximately 1 mL of blood is needed from each of five mice, and the five blood samples are pooled to provide approximately 5 mL.

The blood sample is diluted 1:1 (v/v) with sterile saline, and the blood-saline mixture is layered over Nycoprep separation medium (GIBCO BRL Products) in a 14×75 mm polystyrene test tube at a ratio of approximately 2:1 blood-:Nycoprep. The sample is centrifuged at 500×g for approximately 30 minutes at room temperature. The top layer is removed, leaving ~2–3 mm of the cell band between the top and bottom layers. The remaining cell band is transferred by pipette to a clean centrifuge tube. The cell band is washed with 3 mL of cold phosphate-buffered saline and centrifuged at 400×g for 5 minutes at 4° C. The supernatant is poured off and the pellet is resuspended in ~1 mL of cold phosphate-buffered saline. The suspension is transferred to a 1.5 mL Eppendorf microfuge tube and microfuged at 6600×g for approximately 10 minutes at 4° C. The supernatant is aspirated off and the cell pellet is stored at −70° C.±10° C.

Example 3

Assay to Measure 20S Proteasome Activity in Peripheral White Blood Cells Specific Activity Method The assay is based upon the SDS-inducible chymotrypsin-like activity of free 20S particles. It uses fluorometry to measure the rate at which the 20S proteasome hydrolyzes an amide bond in a small peptide substrate. Measurement of this rate in the absence and in the presence of an inhibitor allows a determination of how enzyme is bound by inhibitor. This assay is used to measure 20S proteasome activity in peripheral white blood cells in mammals, particularly rats, mice, dogs, pigs, rabbits, non-human primates, or human subjects.

Abbreviations and Definitions:

| | |
|---|---|
| AMC | 7-amino-4-methylcoumarin |
| DMF | dimethyl formamide |
| BSA | bovine serum albumin |
| DMSO | dimethyl sulfoxide |
| DTT | dithiothreitol |
| EDTA | disodium ethylenediaminetetraacetate |
| HEPES | N-(2-Hydroxyethyl)piperazine-N-(2-ethanesulfonic acid); pH adjustments with NaOH |
| Hgb | hemoglobin |
| SDS | sodium dodecylsulfate of either - SDS-grade: 99% sodium dodecylsulfate Lauryl grade: ~70% dodecyl sulfate with the remainder as tetradecyl and hexadecyl sulfates. |
| TMB | 3,3',5,5'-tetramethylbenzidine |
| WBC | white blood cells |
| Ys substrate | N-(N-Succinylleucylleucylvalyltyrosyl)-7-amino-4-methylcoumarin (Suc-Leu-Leu-Val-Tyr-AMC) (Bachem) |
| MilliQ water | water purified by reverse osmosis or ion exchange and further treated with a Millipore MilliQ Plus UF water purifying system (or equivalent system) resulting in water with a resistivity greater than 16 MΩ · cm. |

Procedure

The Ys substrate is dissolved to 6 mM in DMSO. A 2% (2 g/100 mL) solution of SDS in MilliQ water is prepared in a glass bottle. The Ys substrate buffer, containing 20 mM HEPES, 0.5 mM EDTA, 0.035% SDS, 1% DMSO, and 60 $\mu$M Ys substrate, is prepared. The final pH of the Ys buffer is 8.0.

Purified 20S proteasome standard from rabbit reticulocytes, prepared according to the literature procedure (McCormack et al., Biochemistry 37:7792–7800 (1998)), is diluted 1:9 (v/v) in 20 mM HEPES/0.5 mM EDTA (pH 7.8).

To 5 $\mu$L of a 20 mM AMC stock solution in DMF is added 2 mL of DMF. The resultant solution is diluted 1:25 in DMSO to produce a 2 $\mu$M AMC solution. The zero value for Ys substrate buffer is recorded on a fluorometer ($\lambda$em=440 nm; $\lambda$ex=380 nm). To 2 mL of Ys substrate buffer is added 5$\mu$L of AMC every 30 seconds for a total of five times to produce a calibration curve for 0 to 50 pmol of AMC. After each addition, a fluorometer reading is taken with an excitation band width of 10 nm and an emission band width of 20 nm. The slope is the fluorometer calibration.

The 20S proteasome standard is diluted 1:10 in 20 mM HEPES/0.5 mM EDTA (pH 7.8) to form a 12 $\mu$g/mL stock solution and placed on ice. 10 $\mu$L of the standard 20S proteasome solution is added to a cuvette containing 2 mL of Ys substrate buffer and the reaction is run for 10 minutes. The maximum linear slope is measured on a fluorometer and provides a calibration of Ys substrate buffer and the assay conditions (Ys calibration). This value is divided by the fluorometer calibration to provide the standardized activity of standard 20S proteasome.

White blood cells, prepared as described in Example 1, are lysed by adding 200 $\mu$L of 5 mM EDTA to each sample. The samples are allowed to stand on ice for at least 15 minutes.

Bradford protein assay (measuring total protein content) and hemoglobin assay are performed on the test sample following standard procedures using commercially available kits. The accurate measure of white blood cell 20S proteasome activity cannot be determined if the hemoglobin content is greater than 10% that of total protein. In this situation, the sample should be treated as a whole blood cell lysate.

10 $\mu$L of a test sample is added to a cuvette containing 2 mL of Ys substrate buffer at 37° C., and the reaction is allowed to run for 10 minutes. Complete activation of the 20S proteasome is achieved within 10 minutes. Consistent results are obtained for readings taken after 4 minutes and up to 10 minutes. The maximum linear slope for at least 1 minute of data is measured. If the rate is less than 1 pmol AMC/sec, the measurement is repeated using 20 µL of the test sample.

The amount of 20S proteasome activity in the test sample is calculated according to the following formula:

$$20S \text{ activity} = \frac{\text{Rate (FU/min)} * \text{fluorometer calibration (pmol/FU)}}{0.0001 * \text{WBC protein (mg)} * 60 \text{ s/min} * Y_s \text{ calibration (pmol/s)}}$$

In order for the assay to be considered valid, the hemoglobin present in the sample must be less than 10% of the total protein, and triplicate 20S proteasome activity values must have a standard deviation of no more than 3%.

Example 4

Derivation of Equation Relating Chymotryptic:tryptic Activity Ratio to Percent Inhibition by a Proteasome Inhibitor Let $k_c$ and $k_t$ be the apparent rate constants for the chymotryptic and tryptic sites, respectively, under standard assay conditions (no inhibitor):

$$v_c = k_c [20S]_t \quad (1)$$

$$v_t = k_t [20S]_t \quad (2)$$

where $[20S]_t$=total proteasome concentration.

In the presence of a proteasome modifier that results in formation of an E I complex, the rate constant for chymotryptic and tryptic sites may be altered by the single molecule of modifier binding to an unidentified site. This effect can be represented by $\beta_c k_c$ and $\beta_t k_t$ where $\beta$=0 indicates total inhibition by the modifier
  (i.e., E I complex has no activity)
$\beta$<1 indicates partial inhibition
  (i.e., E I complex has less activity than E
$\beta$=1 indicates no inhibition
  (i.e., E I complex has the same activity as E)
and $\beta$>1 indicates activation
  (i.e., E I complex has more activity than E).

At a given fraction of modified proteasome (f):

$$v_c = k_c[20S]_t(1-f) + \beta_c k_c[20S]_t(f) \quad (3)$$

$$v_t = k_t[20S]_t(1-f) + \beta_t k_t[20S]_t(f) \quad (4)$$

$$f = \frac{\left(\frac{k_c}{k_t} - \frac{v_c}{v_t}\right)}{\frac{k_c}{k_t} - \frac{v_c}{v_t} + \beta_t \frac{v_c}{v_t} - \beta_c \frac{k_c}{k_t}} \quad \text{Then,} \quad (6)$$

$$\frac{v_c}{v_t} = \frac{k_c}{k_t}\left(\frac{1 - f + \beta_c f}{1 - f + \beta_t f}\right) \quad \text{and} \quad (5)$$

The parameter $k_c/k_t$ is an experimentally determinable constant, at least within an individual and possibly across a species. $k_c/k_t$ is dependent on the assay conditions for measurement of the chymotryptic and tryptic activities, but is not dependent on the identity of the inhibitor. The parameters $\beta_c$ and $\beta_t$ are constants for a particular inhibitor. Their dependence on assay conditions is expected to be much less than $k_c/k_t$ since the inhibitor-enzyme complex activity must be altered in activity differentially from the free enzyme activity. If $\beta$=0 or 1, there is expected to be no dependence of $\beta$ on assay conditions. Once $k_c/k_t$, $\beta_c$, and $\beta_t$ are known under a particular set of assay conditions and inhibitor, the chymotryptic and tryptic activities of a crude sample can be used to calculate the fraction of modified proteasome.

In the specific case of N-(pyrazine)carbonyl-L-phenylalanine-L-leucine boronic acid, $\beta_c$=0, so $$\frac{v_c}{v_t} = \frac{k_c}{k_t}\left(\frac{1 - f}{1 - f + \beta_t f}\right) \quad (8)$$

Analogous equations can be derived for expression of proteasome inhibition as a function of the ratio of any two peptidase activities of the proteasome.

Example 5

Assay to Measure 20S Proteasome Activity in Peripheral White Blood Cells Ratio of Chymotryptic to Tryptic Activity The assay is based upon the SDS-inducible chymotrypsin-like and trypsin-like activities of free 20S proteasome particles. It uses fluorometry to measure the rate at which the 20S proteasome hydrolyzes an amide bond in a small peptide substrate. Since some inhibitors of 20S proteasome ctivity completely inhibit the chymotrypsin-like activity but activate the trypsin-like activity, the percent of 20S proteasome bound by such an inhibitor can be directly determined by the ratio of the chymotrypsin-like and trypsin-like activities.

Abbreviations and Definitions:
In addition to the definitions set forth in Example 3, the following definition also applies:
  Rs substrate N-(N-benzoylvalylglycylarginyl)-7-amino-4-methylcoumarin (Bz-Val-Gly-Arg-AMC) (Bachem)

Procedure

The Ys substrate buffer is prepared as described in Example 3.

The Rs substrate is dissolved to 10 mM in DMSO. The Rs substrate buffer, containing 20 mM HEPES, 0.5 mM EDTA, 0.6% DMSO, and 60 µM Rs substrate, is prepared.

Purified 20S proteasome standard from rabbit reticulocytes, prepared according to the literature procedure (McCormack et al., Biochemistry 37:7792–7800 (1998)), is diluted 1:9 (v/v) in 20 mM HEPES/0.5 mM EDTA (pH 7.8).

Fluorometer calibration is performed as described in Example 3.

Ys substrate buffer calibration is performed as described in Example 3.

Rs substrate buffer calibration is performed in an analogous fashion, substituting Rs substrate buffer for the Ys substrate buffer.

10 µL of a test sample is added to a cuvette containing 2 mL of Ys substrate buffer at 37° C., and the reaction is allowed to run for 10 minutes. Complete activation of the 20S proteasome is achieved within 10 minutes. Consistent results are obtained for readings taken after 4 minutes and up to 10 minutes. The maximum linear slope for at least 1 minute of data is measured. If the rate is less than 1 pmol AMC/sec, the measurement is repeated using 20 µL of the test sample.

20 µL of a test sample is added to a cuvette containing 2 mL of Rs substrate buffer at 37° C., and the reaction is allowed to run for 10 minutes. Complete activation of the 20S proteasome is achieved within 10 minutes. Consistent results are obtained for readings taken after 4 minutes and up to 10 minutes. The maximum linear slope for at least 1 minute of data is measured. If the rate is less than 1 pmol AMC/sec, the measurement is repeated using 20 µL of the test sample in 800 µL Rs buffer.

The percent inhibition (%I) is then calculated according to the following equation:

$$\% I = \frac{100 \cdot \left(\frac{k_c}{k_t} - \frac{v_c}{v_t}\right)}{\left(\frac{k_c}{k_t} - \frac{v_c}{v_t} + \beta_t \frac{v_c}{v_t}\right)} \quad (9)$$

where $v_c$=(chymotryptic rate (FU/s))/(volume of sample assayed);
$v_t$=(tryptic rate (FU/s))/(volume of sample assayed);
$k_c/k_t$=average $v_c/v_t$ of 1–3 baseline samples taken from the subject before dosing with the proteasome inhibitor;
$\mu_t$=activation factor determined upon titration of the proteasome inhibitor. For the proteasome inhibitor 1, $\beta_t$=1.28 in human samples.

Example 6

Preparation of Peripheral Whole Blood Cell Lysates for in Vitro Measurement of 20S Proteasome Activity The required amount of blood is collected into a tube containing anticoagulant. Typically, 1 mL of blood is required. The blood is transferred to a 1.5 mL Eppendorf microfuge tube and microfuged at 6600×g for approximately 10 minutes at 4° C. The plasma is aspirated off and the cell pellet is resuspended 1:1 in a volume (~0.5 mL) of cold phosphate-buffered saline. The cell suspension is again microcentrifuged at 6600×g for approximately 10 minutes at 4° C. The supernatant is aspirated off. 10 µL of cell pellet is transferred to a 1.5 mL Eppendorf microfuge tube and 0.5 mL of 5 mM EDTA is added. The remaining cell pellet is frozen at −70° C. 10–20 µL of this sample is used in the assay (typical protein concentration is 5 mg/mL).

Example 7

Assay to Measure 20S Proteasome Activity in Peripheral Whole Blood Cells Ratio of Chymotryptic-like Activity to Tryptic-like Activity Abbreviations and Definitions:
The abbreviations and definitions set forth in Examples 3 and 5 apply.

PROCEDURE

The Ys substrate is dissolved to 6 mM in DMSO. A 2% (2 g/100 mL) solution of SDS in MilliQ water is prepared in a glass bottle. The Ys substrate buffer, containing 20 mM HEPES, 0.5 mM EDTA, 0.05% SDS, 1% DMSO, and 60 µM Ys substrate, is prepared. The final pH of the Ys buffer is 8.0.

The Rs substrate is dissolved to 10 mM in DMSO. The Rs substrate buffer, containing 20 mM HEPES, 0.5 mM EDTA, 0.6% DMSO, and 60 pM Rs substrate, is prepared. The final pH of the Rs buffer is 8.0.

Standard whole blood lysate is prepared as described in Example 6 and diluted 1:9 in 20 mM HEPES/0.5 EDTA (pH 7.8).

Fluorometer calibration is performed as described in Example 3, using standard whole blood lysate in place of 20S proteasome standard.

Ys substrate buffer calibration is performed as described in Example 3, using standard whole blood lysate in place of 20S proteasome standard.

Rs substrate buffer calibration is performed in an analogous fashion, substituting Rs substrate buffer for the Ys substrate buffer.

A test sample containing 60 µg of protein is added to a cuvette containing 2 mL of Ys substrate uffer at 37° C., and the reaction is allowed to run for 10 minutes. Complete activation of the 20S roteasome is achieved within 10 minutes. Consistent results are obtained for readings taken after 4 minutes and up to 10 minutes. The maximum linear slope for at least 1 minute of data is measured. If the rate is less than 1 pmol AMC/sec, the measurement is repeated, increasing the amount of the test sample to 120 µg of protein.

A test sample containing 60 µg of protein is added to a cuvette containing 2 mL of Rs substrate buffer at 37° C., and the reaction is allowed to run for 10 minutes. Complete activation of the 20S proteasome is achieved within 10 minutes. Consistent results are obtained for readings taken after 4 minutes and up to 10 minutes. The maximum linear slope for at least 1 minute of data is measured. If the rate is less than 1 pmol AMC/sec, the measurement is repeated using 120 µg of the test sample.

The percent inhibition (%I) is then calculated according to the following equation:

$$\% I = \frac{100 \cdot \left(\frac{k_c}{k_t} - \frac{v_c}{v_t}\right)}{\left(\frac{k_c}{k_t} - \frac{v_c}{v_t} + \beta_t \frac{v_c}{v_t}\right)} \quad (9)$$

where $v_c$=(chymotryptic rate (FU/s))/(volume of sample assayed);
$v_t$=(tryptic rate (FU/s))/(volume of sample assayed);
$k_c/k_t$=average $v_c/v_t$ of 1–3 baseline samples taken from the subject before dosing with the proteasome inhibitor;
$\beta_t$=activation factor determined upon titration of the proteasome inhibitor. For the proteasome inhibitor 1, $\beta_t$=1.28 in human samples.

Example 8

Proteasome Activity Levels in Peripheral White Blood Cells of Human Volunteers

Methods

Blood samples (approximately 2 mL each) were obtained on five occasions from seven human volunteers over a period of ten weeks. After collection, white blood cells were isolated from the individual blood samples using a Nycoprep. The resulting pellet was stored in a freezer set to maintain −60° C. to −80° C. until the day of testing. Samples collected on each occasion were tested together and each sample was tested in duplicate.

20S proteasome activity was determined by measuring the rate of proteolytic hydrolysis of a fluorescent(AMC)-tagged peptide substrate by the sample and normalizing the activity to the amount of protein present in the lysate. 5 µL of sample was added to a cuvette containing 2 mL of assay reaction buffer (20 mM HEPES, 0.5 M EDTA, 0.035% SDS, 60 µM Suc-Leu-Leu-Val-Tyr-AMC in 1.0% DMSO) and magnetic stir bar. The cuvette was placed in a fluorometer and maintained at 37° C. while the amount of hydrolyzed AMC was measured by monitoring the increase in detectable fluorescence over a 5 min period (λem=440 nm; λex=380 nm). A linear regression fit of the reaction progress curve of data collected between 3 and 5 minutes after initiation of the reaction gave the rate of hydrolysis in fluorescent units per second (FU/sec). Protein and hemoglobin concentrations were determined using a modified Bradford assay (Pierce) and a hemoglobin-specific enzymatic-based assay (Sigma), respectively. The total amount of protein measured in the sample was corrected by subtraction of the amount of protein contributed by red blood cells (estimated from the hemoglobin concentration). 20S proteasome activity in the sample was determined from the equation:

$$\text{20S proteasome activity (pmoles AMC/sec/mg protein)} = \frac{(\text{FU/sec})/(5 \times 10^{-6} \text{ mL})(\text{protein } \mu\text{g/mL})}{C}$$

where C=conversion factor equating the amount of fluorescence to the concentration of free AMC (FU/pmole AMC).

Results and Discussion

The average 20S proteasome activity values found for each human volunteer ranged from 15.33 to 40.04 pmol AMC/sec/mg protein (Table 1 and FIG. 1). The activities found across each test day are presented in FIG. 2. The average 20S proteasome activity found in the population was 29.97±0.80 pmol AMC/sec/mg protein.

TABLE 1

20S Proteasome Activity Levels in Human Volunteers

| Volunteer | 20S Proteasome Activity (pmol AMC/sec/mg protein) | |
| --- | --- | --- |
| | Average ± SEM | Range |
| A | 31.05 ± 2.13 | 26.32–35.77 |
| B | 32.77 ± 1.88 | 27.94–40.04 |
| C | 29.33 ± 1.93 | 23.29–34.62 |
| D | 30.90 ± 1.87 | 26.69–34.04 |
| E | 33.91 ± 2.00 | 31.69–37.15 |
| F | 29.66 ± 2.01 | 22.78–34.66 |
| G | 23.07 ± 2.11 | 15.33–31.17 |
| Population Average | 29.97 ± 0.80 | 15.33–40.04 |

Example 9

Temporal 20S Proteasome Activity in Isolated White Blood Cells and Tissues Following Administration of N-(Pyrazine)carbonyl-L-phenylalanine-L-leucine Boronic Acid (1)

General Procedures

Dose formulations of 1 were prepared daily during the course of the study. Dilutions were prepared from a stock solution. The stock solution of 1 was made up in 98% saline (0.9%), 2% ethanol with 0.1% ascorbic acid. Dilutions of the stock were made in the same vehicle.

Female CD2-F1 mice (18 to 20 g), female BALB/c mice (18 to 20 g), female Wistar rats (150 to 200 g) and male Sprague-Dawley rats (250 to 450 g) were obtained from Taconic Farms (Germantown, N.Y.). Animals were observed for at least one week and examined for general health before study initiation. Animals used in these studies were asymptomatic. Mice were housed 5 per cage and rats 3 per cage in polycarbonate cages. Corn Cob bedding (AND-1005; Farmers Exchange, Framingham, Mass.) was used during the observation and study periods. Fluorescent lighting was controlled to automatically provide alternate light and dark cycles of approximately 12 hours each. Temperature and humidity were centrally controlled and recorded daily and readings ranged between 21±2° C. and 45±5%, respectively. Pellets of standard rodent chow (#5001, Purina, St. Louis, Mo.) were available ad libitum throughout the observation and study periods. Cambridge city tap water was provided by water bottles ad libitum. No contaminants of food and water are known which would be expected to interfere with the study.

Drugs were administered in vehicle intravenously (IV) using a dose volume of 100 µL per mouse or 1.0 mL/kg in rats. Control groups were administered with the vehicle (98% saline [0.9%], 2% ethanol, 0.1% ascorbic acid). Animals were dosed with 1 as a single IV bolus given either once or on multiple occasions. Animals exhibiting moribund activity were euthanized with $CO_2$ inhalation.

Following IV dosing with 1, blood was withdrawn at various time points and peripheral white blood cells were isolated.

Ex Vivo 20S Proteasome Activity Determined in Peripheral White Blood Cells of Mice After Single Intravenous Administration of 1

In two combined studies, female CD2-F1 mice (18 to 20 g) and female BALB/c mice (18 to 20 g) were administered a single intravenous dose of 1 (0.1 to 3.0 mg/kg in a dose volume of 100 µL). The vehicle was 98% saline [0.9%], 2% ethanol, 0.1% ascorbic acid. Blood samples were collected at 1.0 and 24 h following administration. Due to the blood volume required in the 20S proteasome activity assay, groups of five mice were sacrificed at the same time and their blood pooled to generate single data points.

Figure 3:
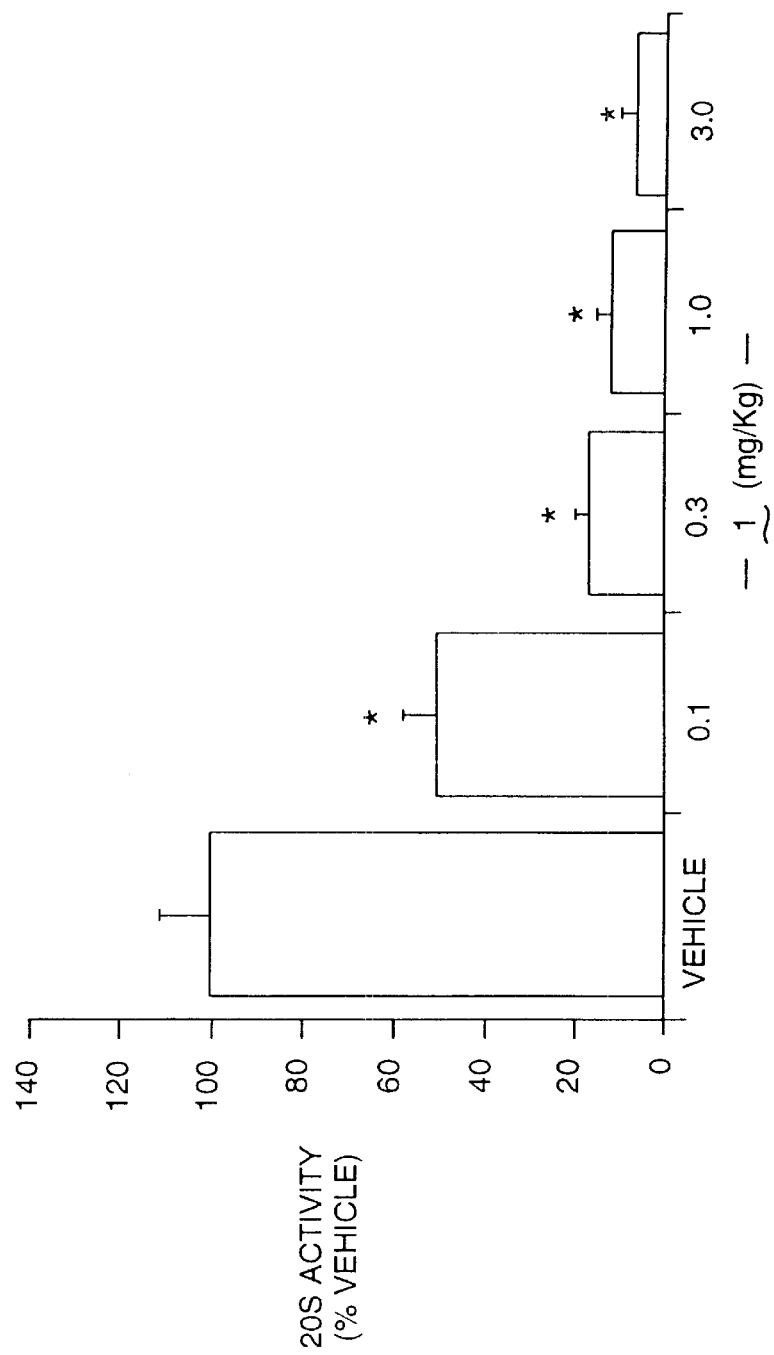
FIG. 3 is a graphical representation of 20S proteasome activity in murine white blood cells 1.0 hour after an intravenous administration of N-(pyrazine)carbonyl-L-phenylalanine-L-leucine boronic acid (1).
Figure 4:
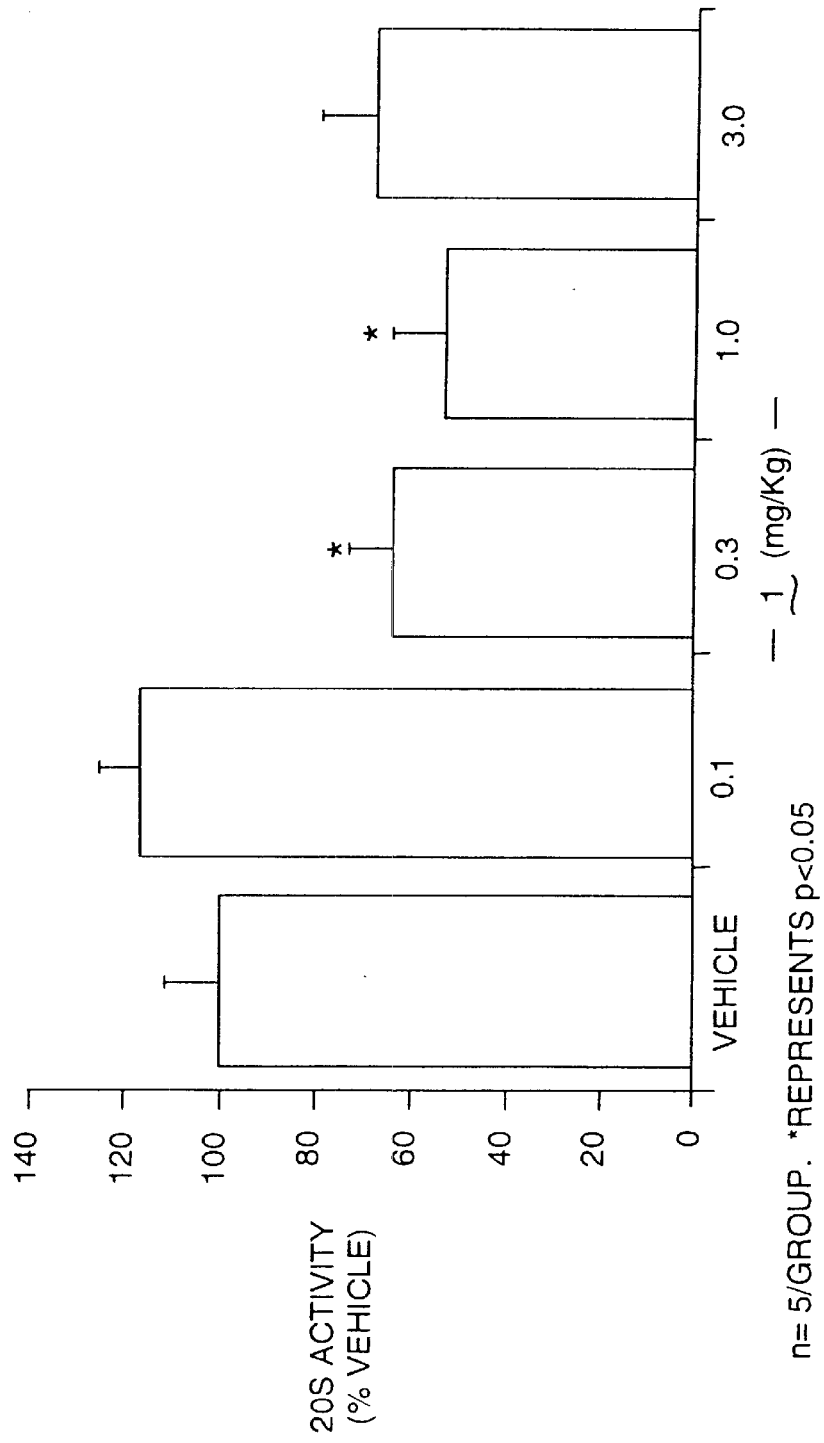
FIG. 4 is a graphical representation of 20S proteasome activity in murine white blood cells 24 hours after an intravenous administration of 1.

There was a significant ($p<0.05$) dose-related decrease in 20S proteasome activity for all dose groups at 1.0 h following intravenous administration of 1 (FIG. 3) which starts to recover at 24 h (FIG. 4). These studies demonstrated a dose-dependent and reversible inhibition of 20S proteasome activity in the peripheral white blood cells of mice following administration of a single intravenous injection of 1.

Ex Vivo 20S Proteasome Activity Determined in Peripheral White Blood Cells of Rats After Single Intravenous Administration of 1

In four combined studies, female Wistar rats (150 to 200 g) were administered a single intravenous dose of 1 (0.03 to 0.3 mg/kg in a dose volume of 1.0 mL/kg). The vehicle was 0.1% ascorbic acid/2% ethanol/98% saline (0.9%). Blood samples were collected at 1.0, 24 and 48 h following administration of 1.

Figure 5:
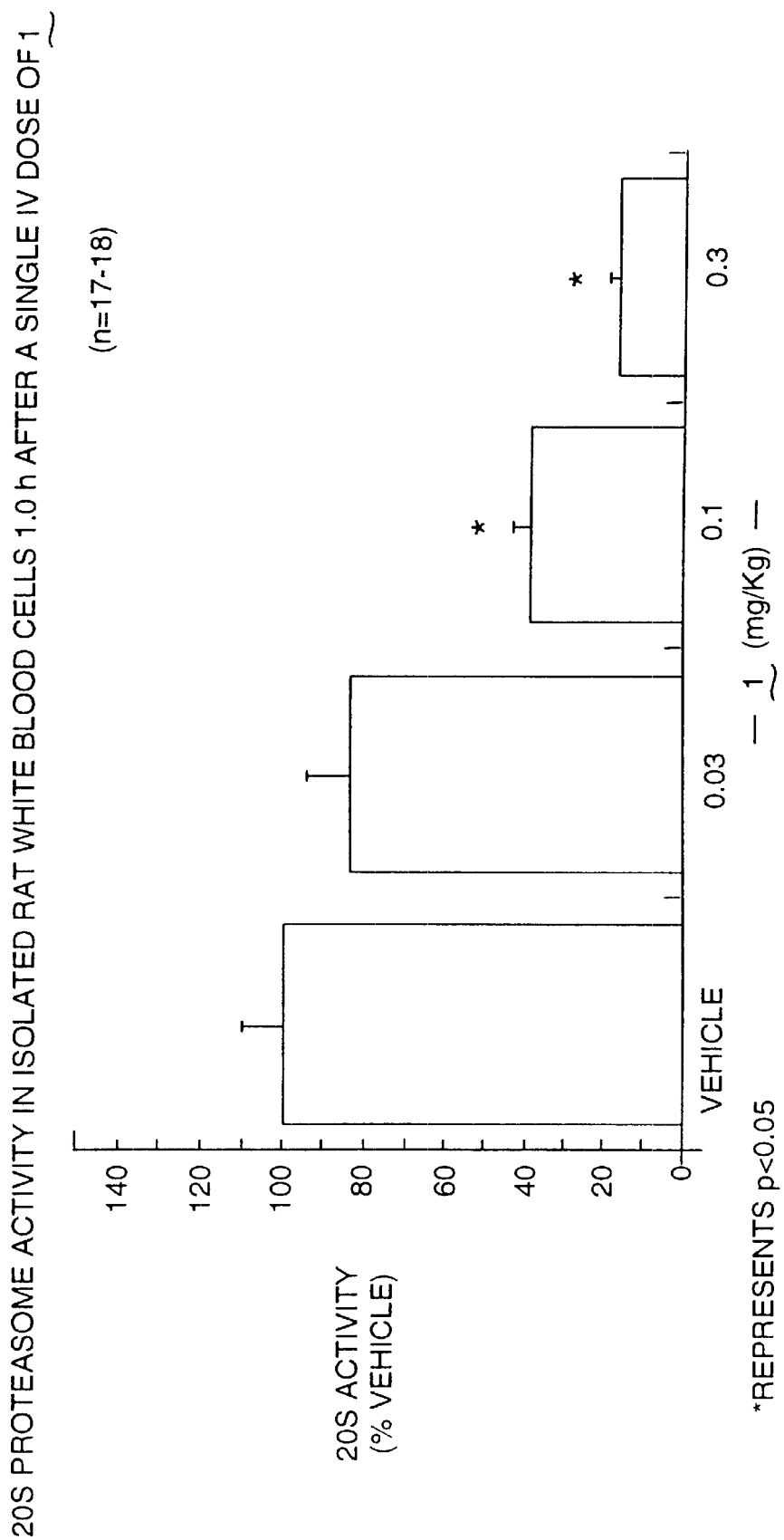
FIG. 5 is a graphical representation of 20S proteasome activity in rat white blood cells 1.0 hour after an intravenous administration of 1.
Figure 6:
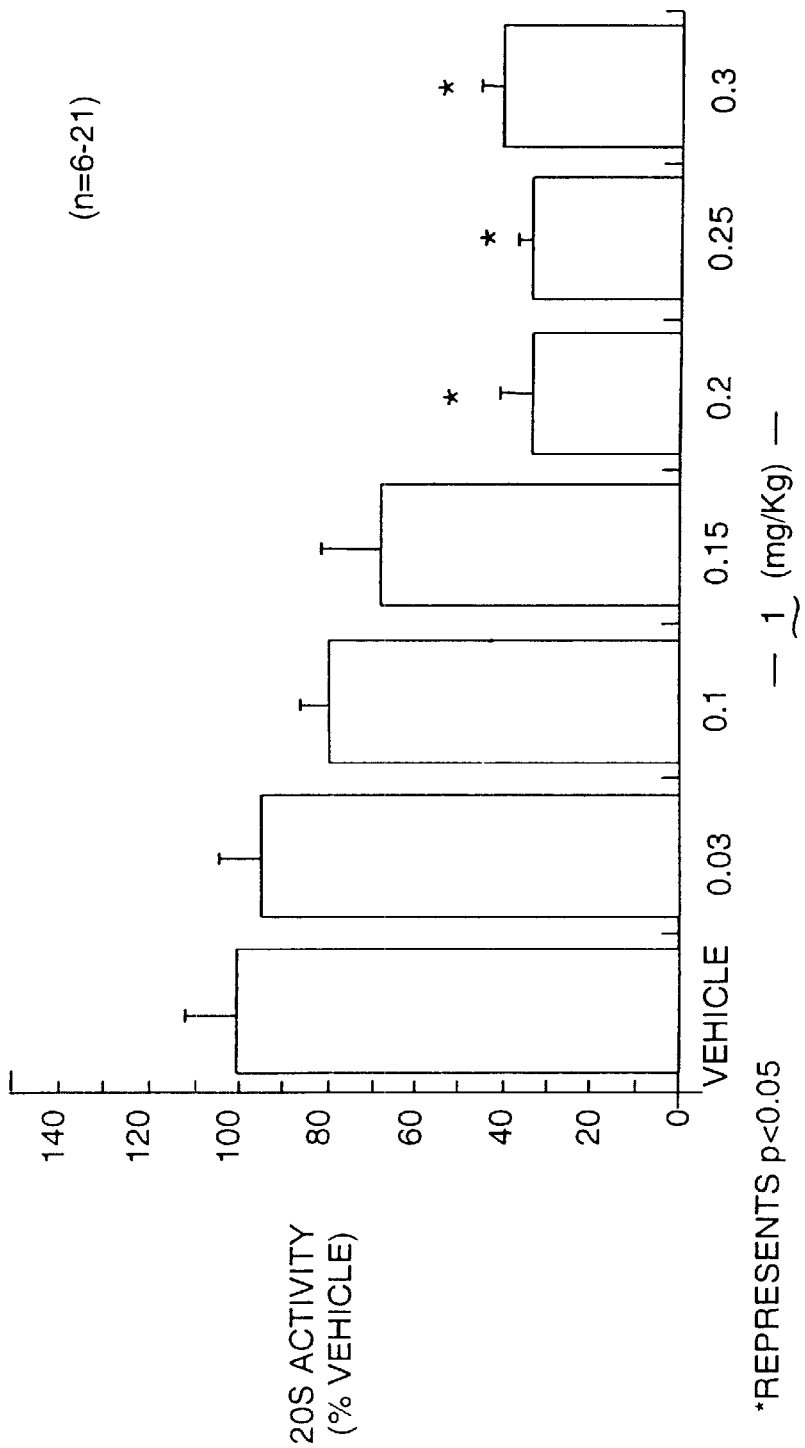
FIG. 6 is a graphical representation of 20S proteasome activity in rat white blood cells 24 hours after an intravenous administration of 1.
Figure 7:
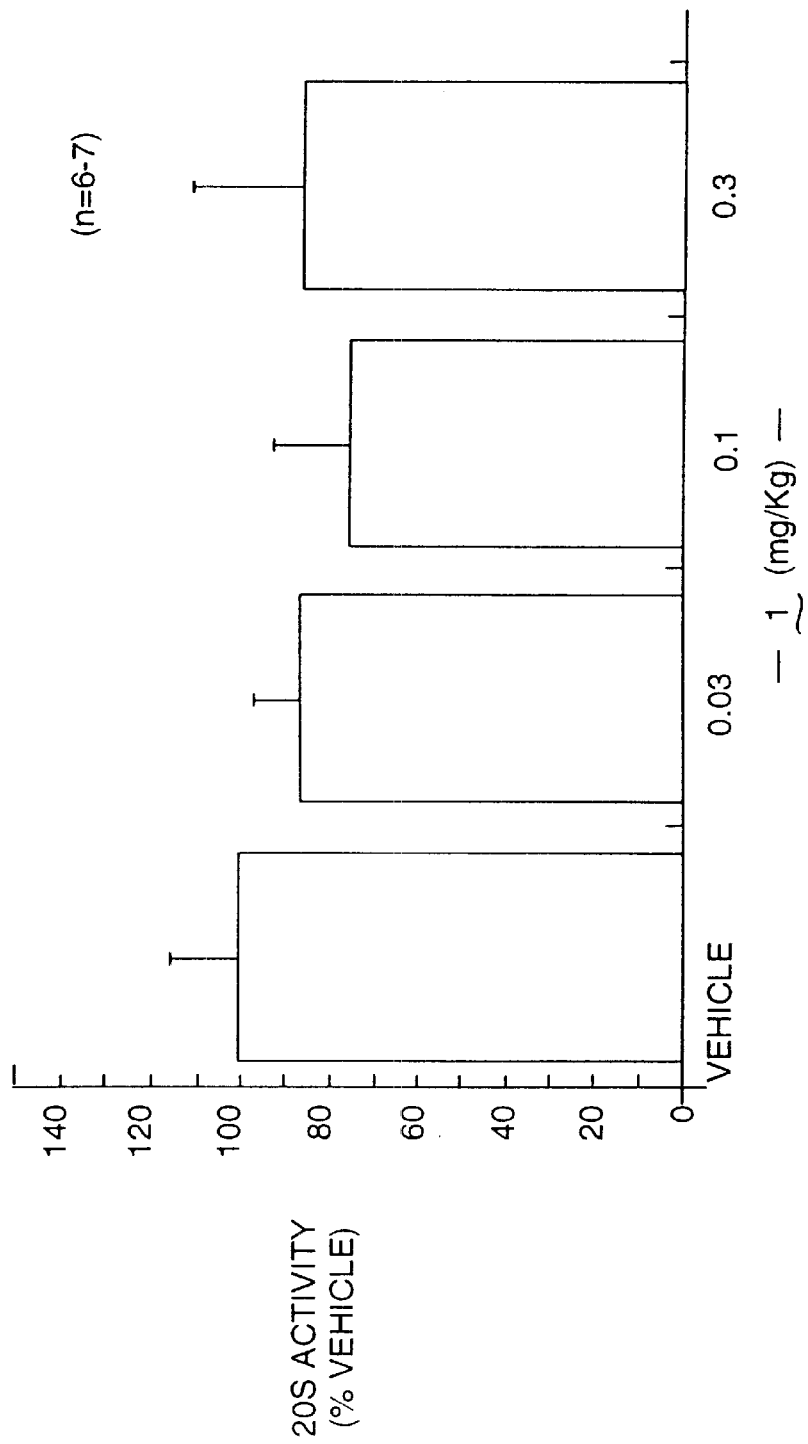
FIG. 7 is a graphical representation of 20S proteasome activity in rat white blood cells 48 hours after an intravenous administration of 1.

There was a significant ($p<0.05$) dose-related decrease in 20S proteasome activity at 1.0 h following intravenous administration of 1 (FIG. 5). Twenty-four hours after administration, the dose-related decreases in 20S proteasome activity were smaller, but remained significant ($p<0.05$) in the higher dose groups, (0.2 mg/kg (FIG. 6). At 48 h after administration, 20S proteasome activity was no longer significantly decreased (FIG. 7).

These studies demonstrated a dose-dependent and reversible inhibition of 20S proteasome activity in the peripheral white blood cells of rats following administration of a single intravenous injection of 1. A slower rate of return to baseline for 20S proteasome activity levels was observed in rats, possibly indicating faster metabolism of 1 in mice.

Ex Vivo 20S Proteasome Activity Determined in Peripheral White Blood Cells of Rats After Repeat Intravenous Administration of 1

When daily intravenous 1 was administered for 7 days, a dose-related decrease in 20S proteasome activity was observed 24 h after administration of the last dose. Significant inhibition was observed for doses $\geq 0.05$ mg/kg. The extent of 20S proteasome inhibition observed 24 h after administration of 7 daily intravenous doses was greater than that observed 24 h after administration of a single intravenous dose and probably reflects a cumulative effect of daily administration of 1 on its biological target, the proteasome.

A significant dose-related decrease in 20S proteasome activity was observed 24 h after administration of the last dose for alternate daily intravenous administration of 1 for 14 days. The dose-related decreases in 20S proteasome activity were significant (p<0.05) in the dose groups ≧0.2 mg/kg. A significant (p<0.05) dose-related decrease in 20S proteasome activity was also observed 24 h after administration of the last dose for once weekly intravenous administration of 1 for 8 weeks. The dose-related decreases in 20S proteasome activity were significant (p<0.05) in the dose groups ≧h 0.1 mg/kg.

In an additional repeat dose study, male Sprague-Dawley rats (250 to 450 g; n=6 per group) were treated with twice weekly intravenous doses of 1 (0.01 to 0.35 mg/kg/day in a dose volume of 1.0 mL/kg) for two weeks. The vehicle was 0.1% ascorbic acid/2% ethanol/98% saline (0.9%). Blood samples were collected 1.0 h after the last dose for evaluation of 20S proteasome activity.

Figure 8:
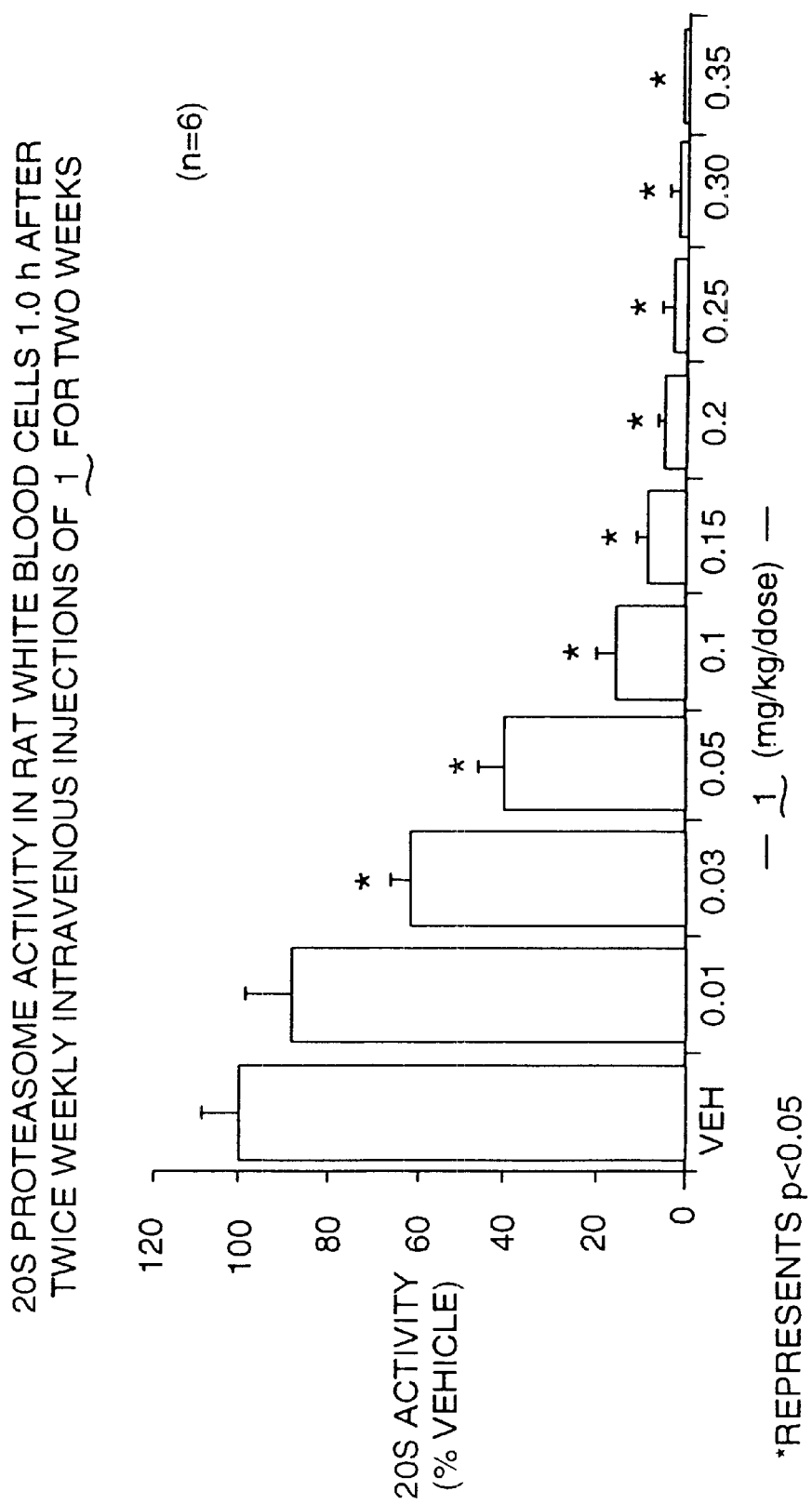
FIG. 8 is a graphical representation of 20S proteasome activity in rat white blood cells 1.0 hour after twice weekly intravenous injections of 1 for two weeks.

When 1 was administered twice weekly for 2 weeks (total of 4 doses), a dose-related decrease in 20S proteasome activity was observed 1.0 h after the last dose (FIG. 8). The dose-related decreases in 20S proteasome activity were significant (p<0.05) for all dose groups ≧0.03 mg/kg.

The results indicate that repeat dose administration of 1 elicits a dose-related decrease in 20S proteasome activity in rat white blood cells. The extent of inhibition of 20S proteasome activity is greater than that seen after a single dose when 1 is given daily or every other day. When the interval between doses of 1 is increased to allow for recovery (i.e., once weekly regimens), the degree of inhibition is equivalent to single administration of 1. This pharmacodynamic profile supports twice weekly dosing with 1, wherein transient inhibition is observed.

Ex Vivo 20S Proteasome Activity Determined in Rat Tissues After Repeat Intravenous Administration of 1

In two studies, female Wistar rats (150 to 200 g) were administered a single intravenous dose of 1 (0.03, 0.1 and 0.3 mg/kg in a dose volume of 1.0 mL/kg). The vehicle was 0.1% ascorbic acid/2% ethanol/98% saline (0.9%). Tissue samples were collected from liver and brain at 1.0, 24 and 48 h following administration for evaluation of 20S proteasome activity.

There was a significant (p<0.05) dose-related decrease in 20S proteasome activity in rat liver at 1.0 h following intravenous administration of 1. Twenty-four hours after administration, the dose-related decreases in 20S proteasome activity were smaller, but remained significant (p<0.05) in the high dose group, 0.3 mg/kg. At 48 h after administration, the 20S proteasome activity in rat liver had returned to baseline. The extent of 20S proteasome inhibition in the liver returned to baseline levels faster than that observed for peripheral white blood cells. No 20S proteasome inhibition was observed in brain tissue, reflecting the lack of penetration of 1 into this tissue.

In a third study, male Sprague-Dawley rats (250 to 450 g) were administered a single intravenous dose of 1 (0.1 and 0.3 mg/kg in a dose volume of 1.0 mL/kg). The vehicle was 0.1% ascorbic acid/2% ethanol/98% saline (0.9%). Blood and tissue samples were collected 1.0 h following administration for evaluation of 20S proteasome activity. The tissues collected were brain, colon, liver, muscle (gastrocnemius), prostate and testes.

Significant (p<0.05) dose-related decreases in 20S proteasome activity were observed in peripheral white blood cells, colon, liver, muscle (gastrocnemius), and prostate at 1.0 h following intravenous administration of 1. No 20S proteasome inhibition was observed in brain and testes, reflecting the lack of 1 penetration into these tissues.

The 20S proteasome inhibition in tissues 1.0 h after intravenous dose administration, except for brain and testes, was similar to that observed for peripheral white blood cells.

Ex Vivo 20S Proteasome Activity Determined in Primates After Single Intravenous Administration of 1

Male and female Cynomolgus monkeys (2.2 to 3.5 kg) were assigned to four groups (5/sex/group). Each group received 0 (vehicle control), 0.045, 0.067 or 0.100 mg/kg/dose of 1 as a single intravenous injection in a dose volume of 0.3 mL/kg twice weekly for 4 weeks (days 1, 5, 8, 12, 15, 19, 22 and 26). The vehicle was 0.1% ascorbic acid/2% ethanol/98% saline (0.9%). Three males from the control, low- and mid-dose groups, two high-dose males, and three females/group were sacrificed at the end of treatment on Day 27. Two animals/sex/group were designated as recovery animals and received treatment for 4 weeks followed by 2 weeks of recovery; they were sacrificed on Day 41.

Blood was collected for 20S proteasome activity determination prior to treatment, at 1.0 h after dosing on Days 1, 8, 15 and 22, and at 1.0 h prior to dosing on Days 5, 12, 19 and 26; and on Days 31, 34, 38, and 41 (recovery sacrifice animals). Blood was also collected for 20S proteasome activity determination from the high-dose male before it was sacrificed in moribund condition on Day 26 after receiving 8 doses.

Figure 9:
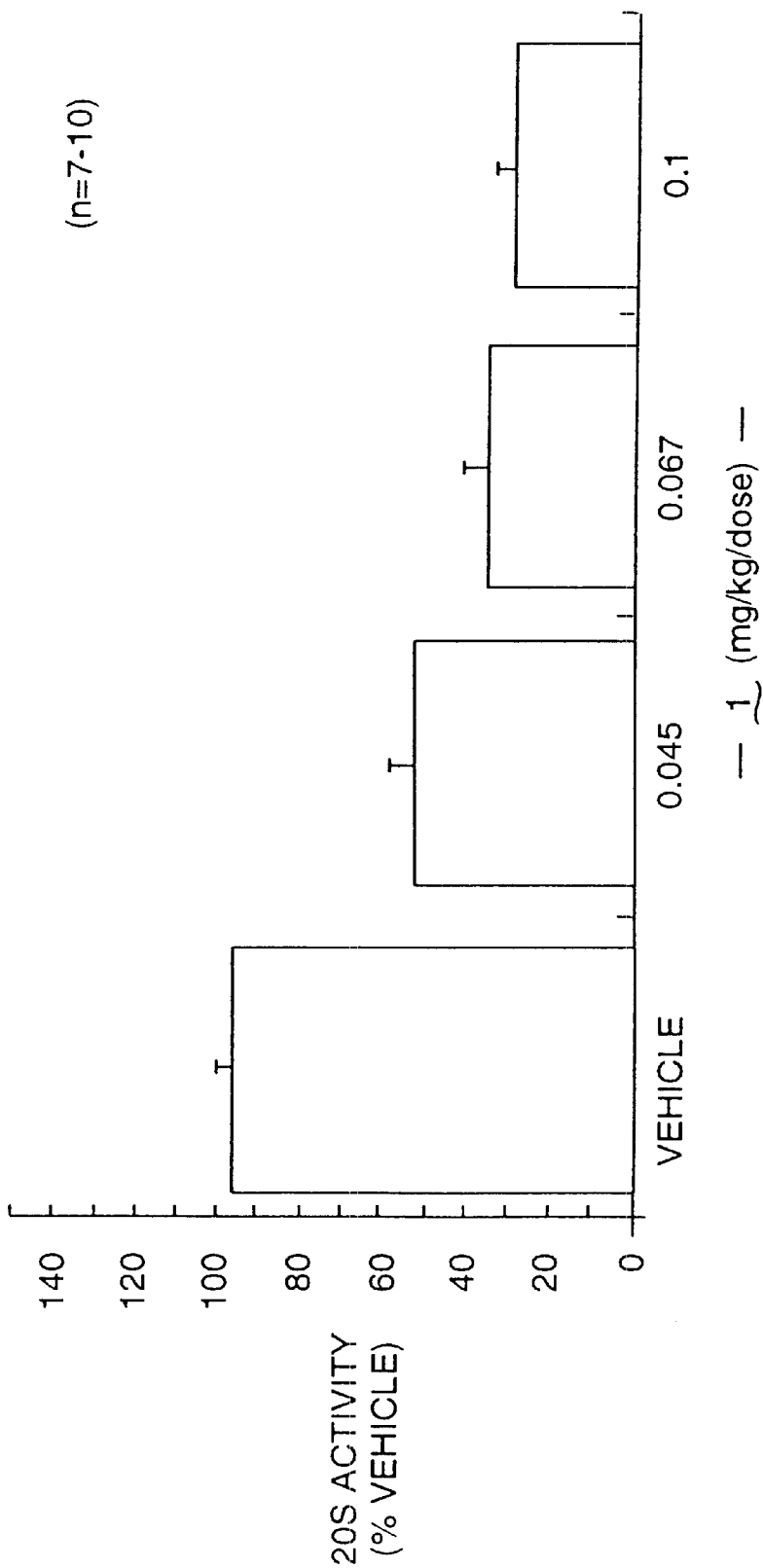
FIG. 9 is a graphical representation of 20S proteasome activity in primate white blood cells 1.0 hour after an intravenous administration of 1.
Figure 10:
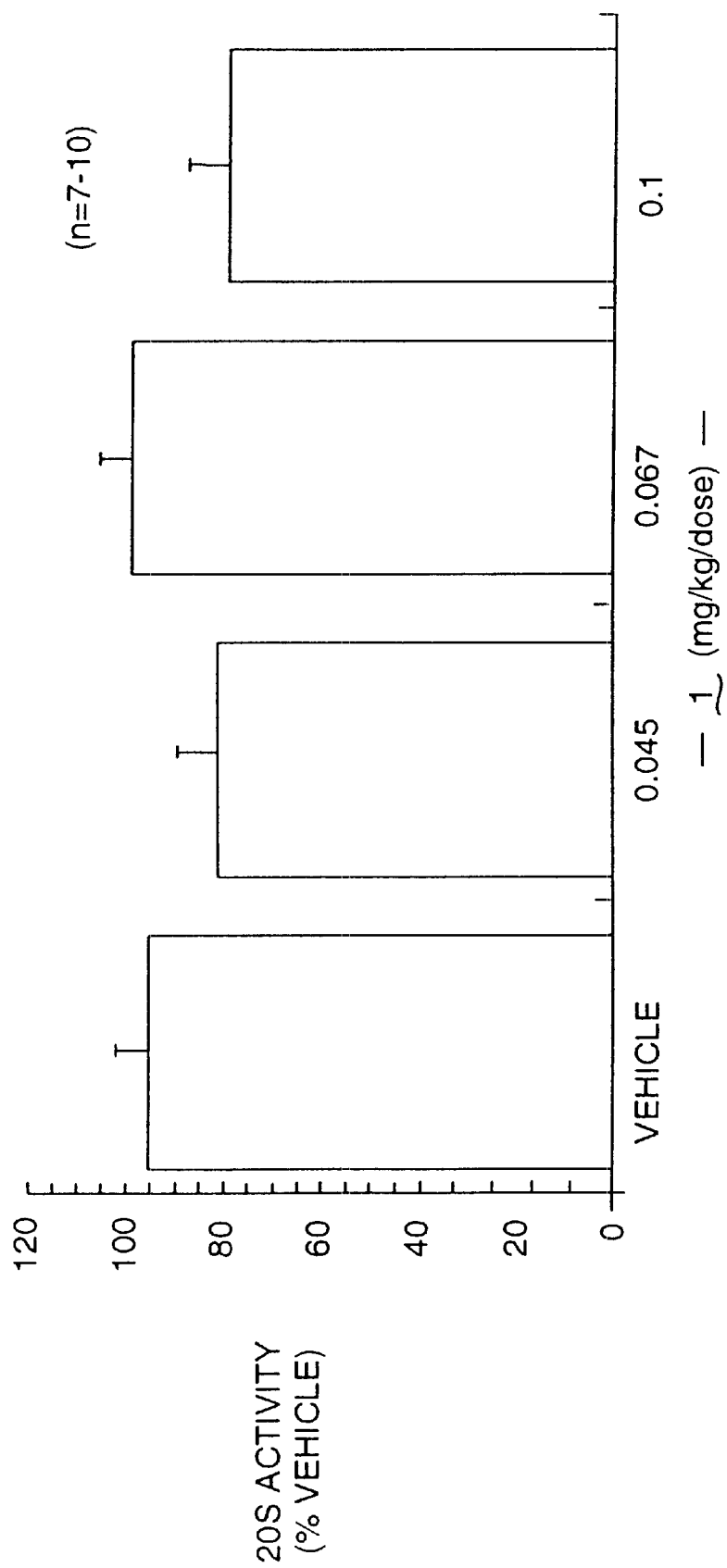
FIG. 10 is a graphical representation of 20S proteasome activity in primate white blood cells 72 hours after an intravenous administration of 1.

Determination of white blood cell 20S proteasome activity 1.0 h after dosing revealed a significant and dose-related decrease in enzyme activity that had recovered by 72 hours, prior to the subsequent dose (FIGS. 9 and 10). The moribund animal was found to have low residual 20S proteasome activity in its white blood cells at sacrifice on Day 26.

These data support a twice weekly treatment regimen for 1, since the 20S proteasome levels recover between doses.

Example 10

Figure 11:
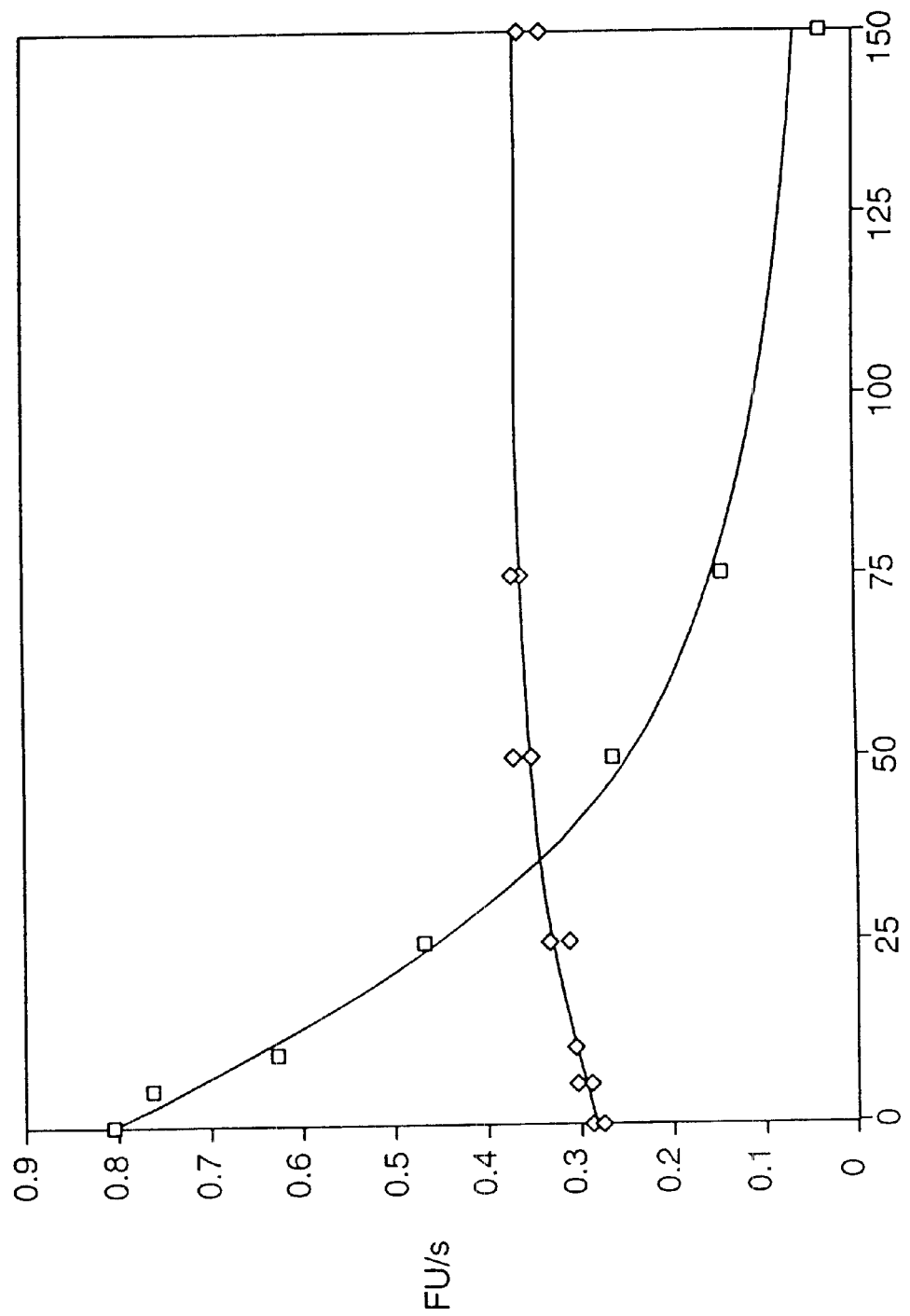
FIG. 11 is a graphical representation of chymotryptic (□) and tryptic (◇) activities as a function of the concentration of 1, demonstrating that 1 fully inhibits chymotryptic activity, but causes an activation of tryptic activity.

Effect of N-(Pyrazine)carbonyl-L-phenylalanine-L-leucine Boronic Acid (1) on the Chymotryptic and Tryptic Activities of Purified 20S Proteasome from Rabbit Reticulocytes 20S Proteasome was purified from rabbit reticulocytes according to published procedures (McCormack et al., Biochemistry 37:7792–7800 (1998)). Chymotryptic and tryptic assays were performed as described in Examples 3 and 5 at increasing concentrations of the proteasome inhibitor 1. Data is presented in FIG. 11.

Example 11

Figure 12:
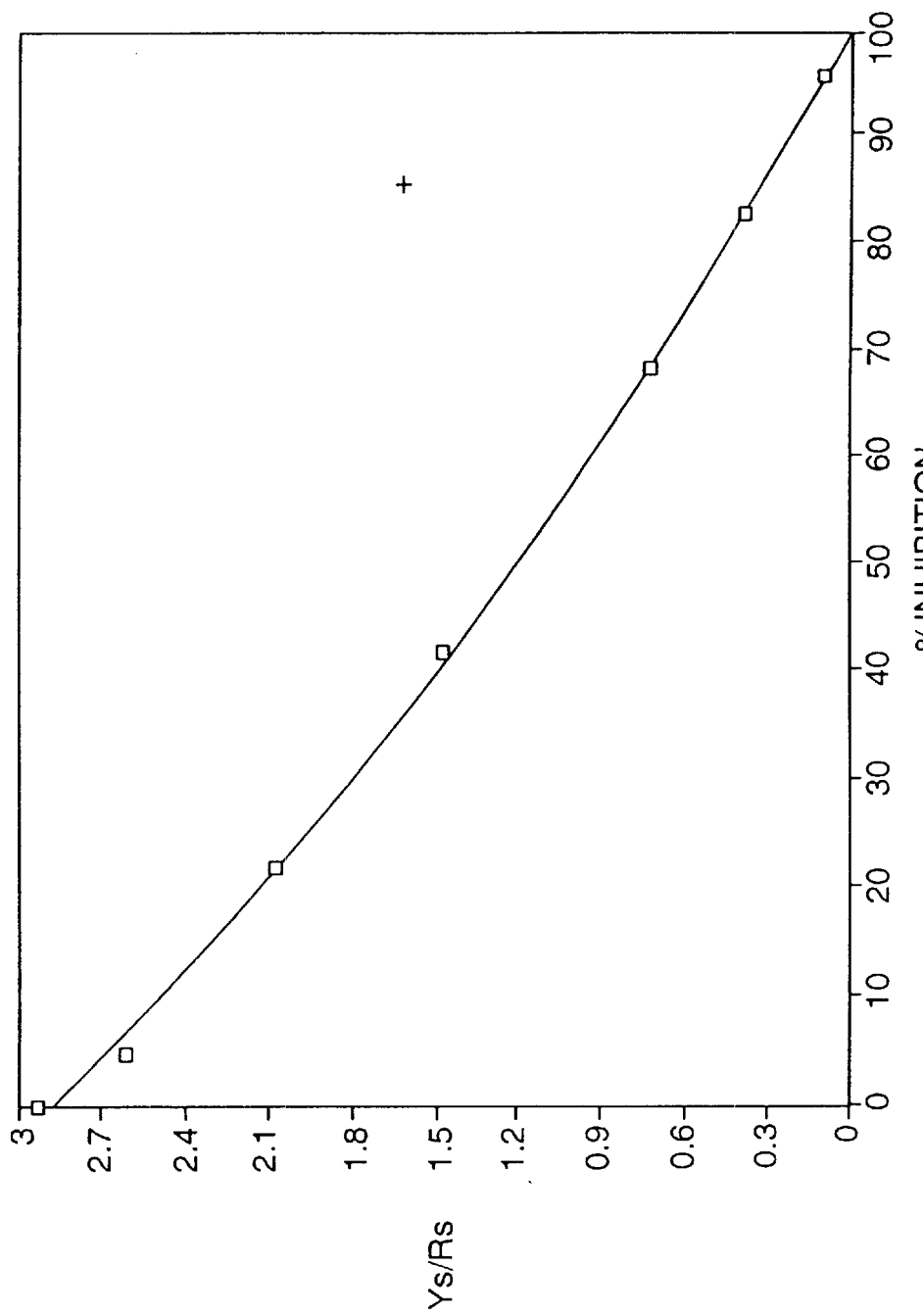
FIG. 12 is a graphical plot comparing percent proteasome inhibition and the ratio of chymotryptic to tryptic activities with purified 20S proteasome from rabbit reticulocytes.

Correlation of Percent Inhibition and Ratio of Chymotryptic Activity to Tryptic Activity in Purified 20S Proteasome From Rabbit Reticulocytes Purified 20S proteasome From rabbit reticulocytes was prepared according to published procedures (McCormack et al., Biochemistry 37:7792–7800 (1998)). Chymotryptic and tryptic assays were performed as described in Examples 3 and 5 at increasing concentrations of the proteasome inhibitor 1. The data was fitted to $v_c/v_t = k_c/k_t * (1-f)/(1-f+\beta_t * f)$, where $k_c/k_t = 2.88 \pm 0.03$, $\beta_t = 1.38 \pm 0.05$, and $\%I = f * 100$ (FIG. 12).

Example 12

Correlation of Percent Inhibition and Ratio of Chymotryptic Activity to Tryptic Activity in Rat White Blood Cell Lysates.

Figure 13:
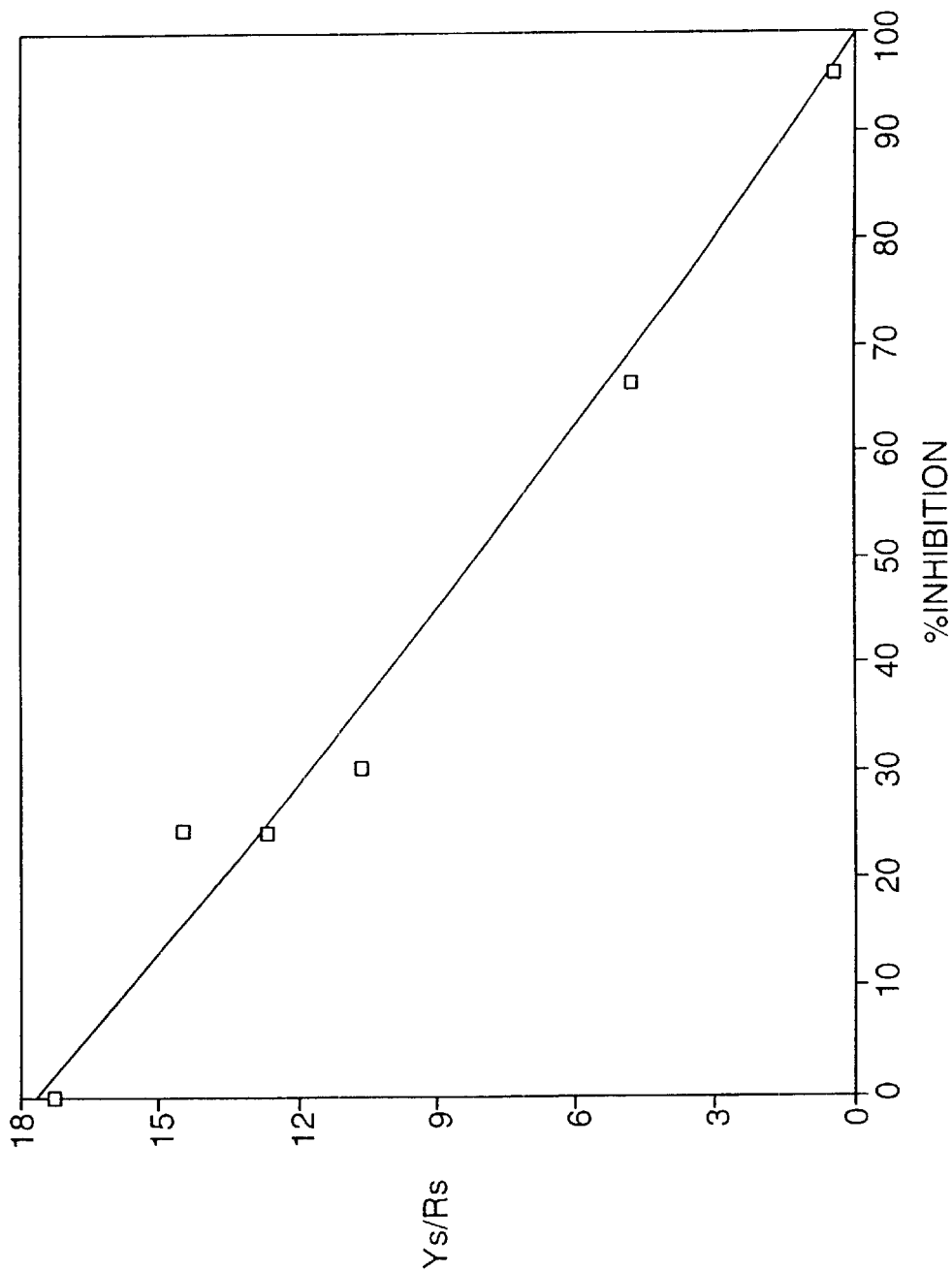
FIG. 13 is a graphical plot comparing percent proteasome inhibition and the ratio of chymotryptic to tryptic activities with rat white blood cell lysates.

Chymotryptic and tryptic assays were performed as described in Examples 3 and 5 at increasing concentrations of the proteasome inhibitor 1. Data was fitted as in Example 10, to give $k_c/k_r=17.6\pm$ and $\beta_r=1.1\pm0.2$ (FIG. 13).

What is claimed is:

1. A method for monitoring pharmacodynamic drug action of a proteasome inhibitor in a mammal, comprising administering the proteasome inhibitor to the mammal; obtaining one or more test biological samples from the mammal at one or more specified times after administering the proteasome inhibitor; performing an assay of proteasome enzymatic activity present in the test biological sample or samples after removal from the mammal; and comparing the amount of proteasome enzymatic activity in the test biological sample to that in a reference biological sample obtained from a mammal to which no proteasome inhibitor has been administered.

2. The method according to claim 1, wherein the biological sample is selected from the group consisting of blood, urine, organ, and tissue samples.

3. The method according to claim 2, wherein the biological sample is a blood sample.

4. The method according to claim 3, wherein the blood sample is a white blood cell lysate.

5. The method according to claim 3, wherein the biological sample is a whole blood cell lysate.

6. The method according to claim 1, wherein the biological sample is selected from the group consisting of tumor biopsies, skin biopsies, colon biopsies, synovial fluid, bronchial fluid, muscle cells, blood cells, and blood cell precursors.

7. The method according to claim 1, wherein the mammal is selected from the group consisting of rats, mice, non-human primates, and humans.

8. The method according to claim 7, wherein the mammal is a human.

9. The method according to claim 1, wherein proteasome activity is measured by assaying the rate of proteolysis in the presence of a 20S proteasome activator.

10. The method according to claim 9, wherein the activator is SDS.

11. The method according to claim 10, wherein the biological sample is a white blood cell lysate, and SDS is present at a concentration of about 0.035%.

12. The method according to claim 10, wherein the biological sample is a whole blood cell lysate, and SDS is present at a concentration of about 0.05%.

13. The method according to claim 1, wherein chymotryptic activity is assayed.

14. The method according to claim 1, wherein tryptic activity is assayed.

15. The method according to claim 1, wherein proteasome activity in the biological sample and proteasome activity in the reference sample are separately normalized relative to protein concentration.

16. The method according to claim 1, wherein proteasome activity in the biological sample and proteasome activity in the reference sample are separately normalized relative to cell count.

17. The method according to claim 1, wherein proteasome activity in the biological sample and proteasome activity in the reference sample are separately determined as a ratio of a first peptidase activity of the proteasome to a second peptidase activity of the proteasome.

18. The method according to claim 17, wherein the first peptidase activity is chymotryptic activity and the second peptidase activity is tryptic activity.

19. The method according to claim 1, wherein the proteasome inhibitor is selected from the group consisting of peptidyl aldehydes, vinyl sulfones, epoxyketones, peptidyl boronic acids, and lactacystin analogs.

20. The method according to claim 19, wherein the proteasome inhibitor is a peptidyl boronic acid.

21. The method according to claim 20, wherein the peptidyl boronic acid is selected from the group consisting of:

N-acetyl-L-leucine-β-(1-naphthyl)-L-alanine-L-leucine boronic acid;

N-(8-quinoline)sulfonyl-β-(1-naphthyl)-L-alanine-L-leucine boronic acid;

N-(pyrazine)carbonyl-L-phenylalanine-L-leucine boronic acid;

β-(1-naphthyl)-L-alanine-L-leucine boronic acid; and

N-(4-morpholine)carbonyl-[O-(2-pyridylmethyl)]-L-tyrosine-L-leucine boronic acid.

22. The method according to claim 21, wherein the peptidyl boronic acid is N-(pyrazine)carbonyl-L-phenylalanine-L-leucine boronic acid.

23. The method according to claim 19, wherein the proteasome inhibitor is a lactacystin analog.

24. The method according to claim 23, wherein the lactacystin analog is selected from the group consisting of lactacystin, clasto-lactacystin β-lactone, 7-ethyl-clasto-lactacystin β-lactone and 7-n-propyl-clasto-lactacystin β-lactone.

25. The method according to claim 24, wherein the lactacystin analog is 7-n-propyl-clasto-lactacystin β-lactone.

26. The method according to claim 1, wherein the biological sample is an organ or tissue sample.

27. The method according to claim 26, wherein the proteasome substrate has a detectable label.

28. The method according to claim 26, wherein the proteasome substrate is selected from the group consisting of lysozyme, α-lactalbumin, β-lactoglobulin, insulin b-chain, and ornithine decarboxylase.

29. The method according to claim 26, wherein the proteasome substrate is a peptide less than 10 amino acids in length.

30. The method according to claim 1, wherein a proteasome substrate is provided to the biological sample, and proteasome enzymatic activity is assayed by monitoring proteolytic cleavage of the substrate.

* * * * *

UNITED STATES PATENT AND TRADEMARK OFFICE
CERTIFICATE OF CORRECTION

PATENT NO. : 6,613,541 B1
DATED : September 2, 2003
INVENTOR(S) : Vaddi, Gopalakrishna R. et al.

It is certified that error appears in the above-identified patent and that said Letters Patent is hereby corrected as shown below:

<u>Title page,</u>
Item [75], Inventors, please add the following inventor to the list of inventors:

-- Vincent CHAU, Hershey, PA --

Signed and Sealed this

Twentieth Day of April, 2004

JON W. DUDAS
*Acting Director of the United States Patent and Trademark Office*